United States Patent
Noda (12)

(10) Patent No.: US 10,545,141 B2
(45) Date of Patent: Jan. 28, 2020

(54) IMMUNOASSAY METHOD AND IMMUNOASSAY SYSTEM

(71) Applicant: KONICA MINOLTA, INC., Chiyoda-ku, Tokyo (JP)

(72) Inventor: Tetsuya Noda, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 561 days.

(21) Appl. No.: 15/109,079

(22) PCT Filed: Jan. 7, 2015

(86) PCT No.: PCT/JP2015/050214
§ 371 (c)(1),
(2) Date: Aug. 17, 2016

(87) PCT Pub. No.: WO2015/105114
PCT Pub. Date: Jul. 16, 2015

(65) Prior Publication Data
US 2016/0370364 A1 Dec. 22, 2016

(30) Foreign Application Priority Data
Jan. 10, 2014 (JP) .................................. 2014-003228

(51) Int. Cl.
*G01N 33/543* (2006.01)
*G01N 21/64* (2006.01)

(52) U.S. Cl.
CPC ..... *G01N 33/54373* (2013.01); *G01N 21/648* (2013.01); *G01N 21/6486* (2013.01);
(Continued)

(58) Field of Classification Search
None
See application file for complete search history.

(56) References Cited

U.S. PATENT DOCUMENTS 4,163,643 A * 8/1979 Hunter ............... G01N 35/04
366/109
5,316,726 A * 5/1994 Babson ............. G01N 35/0095
356/418
(Continued)

FOREIGN PATENT DOCUMENTS

JP 05307039 A 11/1993
JP 11316234 A 11/1999
(Continued)

OTHER PUBLICATIONS

Japanese Office Action dated Apr. 17, 2018 issued in counterpart Japanese Application No. 2015-556813.
(Continued)

*Primary Examiner* — Christopher L Chin
(74) *Attorney, Agent, or Firm* — Holtz, Holtz & Volek PC

(57) ABSTRACT

An immunoassay method in which, by using a sensor chip on which a plurality of capture regions which capture a material to be detected by a first capturing body are arranged separated from each other, the material to be detected captured by the first capturing body is individually detected, wherein the plurality of capture regions are formed by using a different type of first capturing body depending on the type of a material to be detected to be captured, the method having: a detection processing order determination step of determining a detection processing order between the capture regions based on information about a detection processing order between the plurality of the capture regions; and a detection processing step of performing a detection processing for each of the capture regions according to the detection processing order between the plurality of the capture regions, and an immunoassay system using the method.

17 Claims, 19 Drawing Sheets

(52) U.S. Cl.
CPC .............. *G01N 2021/6417* (2013.01); *G01N 2201/068* (2013.01); *G01N 2201/06113* (2013.01)

(56) References Cited

U.S. PATENT DOCUMENTS

| | | | | |
|---|---|---|---|---|
| 5,492,840 | A * | 2/1996 | Malmqvist | G01N 21/553 356/317 |
| 7,718,072 | B2 * | 5/2010 | Safar | B01L 3/5082 210/222 |
| 8,383,421 | B2 * | 2/2013 | Yanagida | B01L 3/50851 422/63 |
| 8,592,224 | B2 * | 11/2013 | Staab | B01J 19/0046 435/7.23 |
| 2002/0149775 | A1 | 10/2002 | Mori et al. | |
| 2007/0091306 | A1 | 4/2007 | Berik et al. | |
| 2007/0111301 | A1 * | 5/2007 | Fujita | G01N 35/00029 435/287.2 |
| 2008/0273918 | A1 | 11/2008 | Linder et al. | |
| 2009/0028754 | A1 * | 1/2009 | Robb | B01L 9/06 422/65 |
| 2009/0155793 | A1 | 6/2009 | Oliphant | |
| 2009/0311773 | A1 | 12/2009 | Schick et al. | |

FOREIGN PATENT DOCUMENTS

| | | |
|---|---|---|
| JP | 2002372490 A | 12/2002 |
| JP | 2004239715 A | 8/2004 |
| WO | 2012090759 A1 | 7/2012 |

OTHER PUBLICATIONS

Extended European Search Report dated Aug. 18, 2017 issued in counterpart European Application No. 15735557.9.
International Search Report (ISR) including Written Opinion dated Mar. 31, 2015, issued in counterpart International Application No. PCT/JP2015/050214.
European Office Action dated Sep. 18, 2018 issued in European Application No. 15735557.9.

* cited by examiner

[Fig. 1]
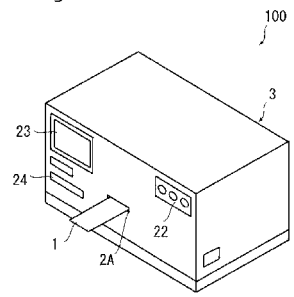
[Fig. 2]
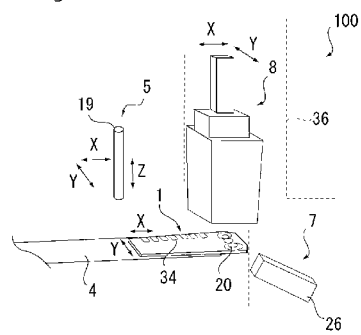
[Fig. 3]
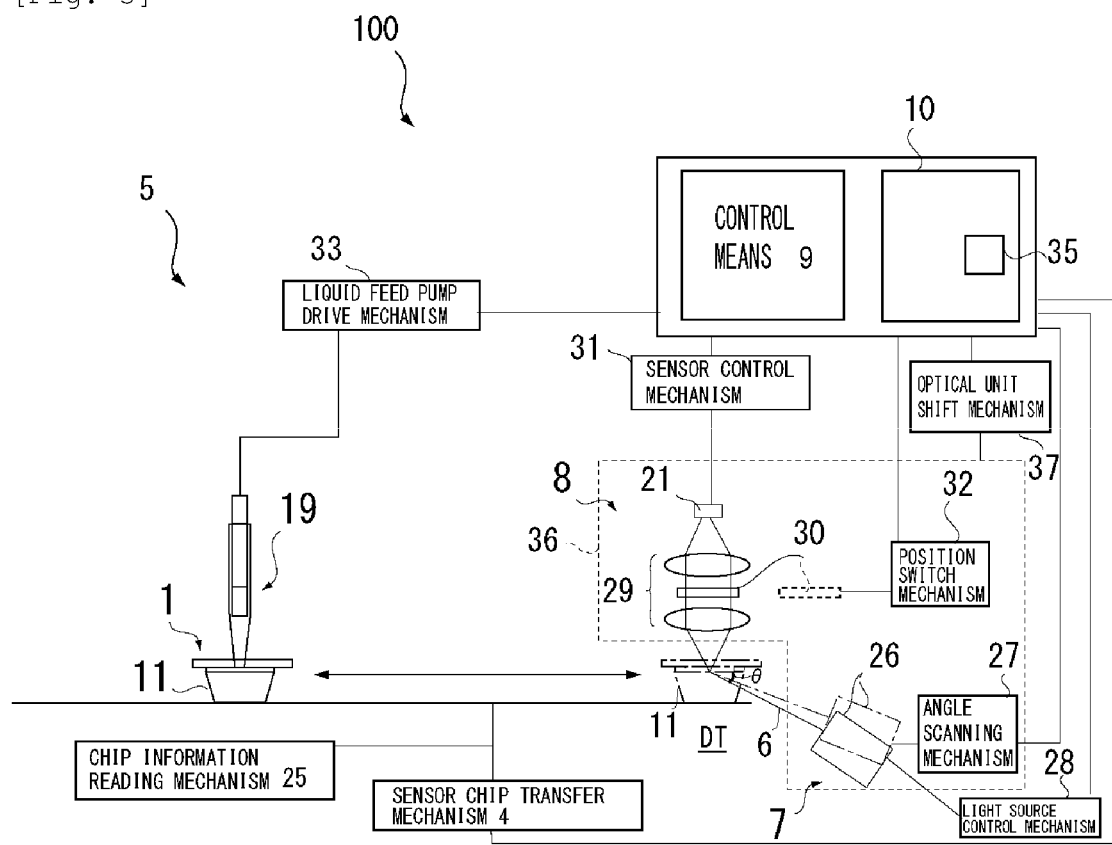

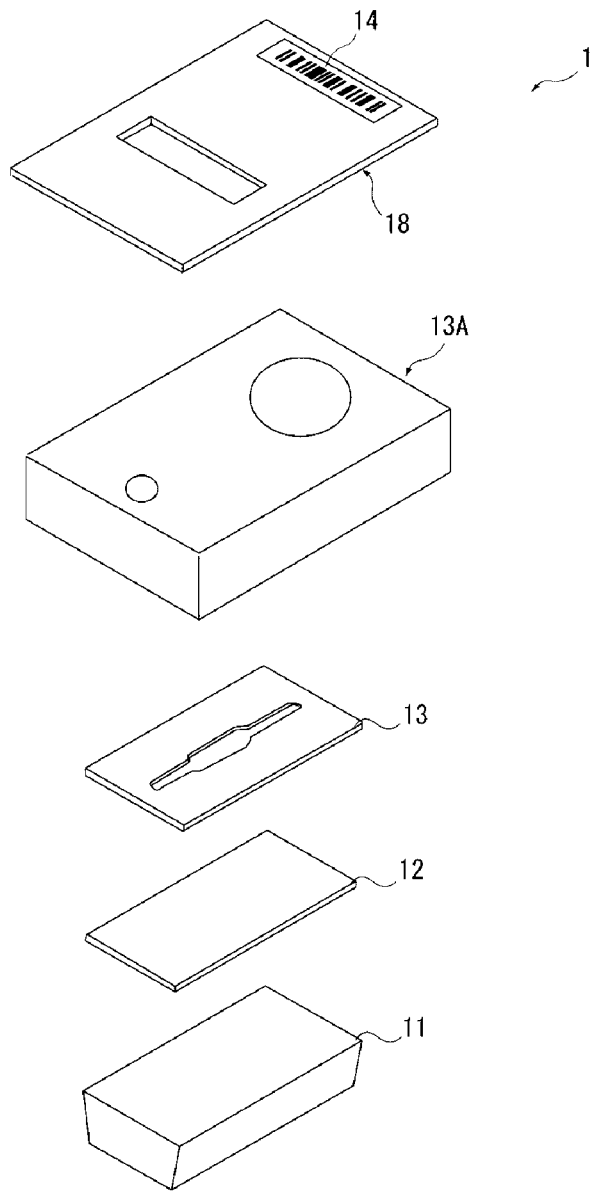
[Fig. 4]

[Fig. 5]
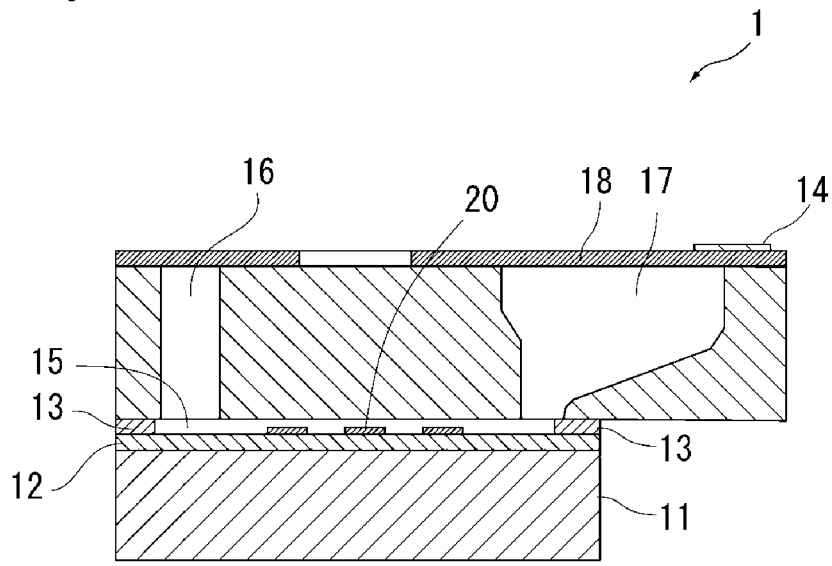
[Fig. 6]
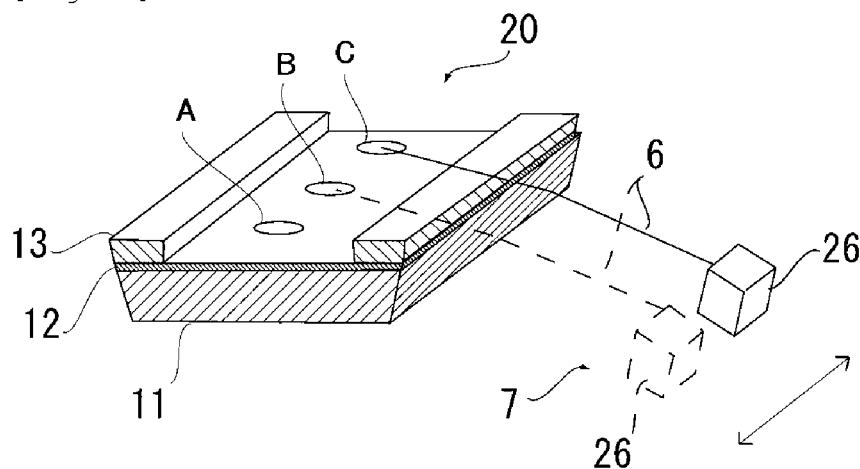
[Fig. 7]
| SPOT ID | NAME OF MATERIAL TO BE DETECTED | DISSOCIATION CONSTANT (mol/L) | | | SPOT POSITION | MEASUREMENT ORDER | MEASUREMENT TIME (SECOND) |
|---|---|---|---|---|---|---|---|
| | | CAPTURE ANTIBODY: MATERIAL TO BE DETECTED | LABELED ANTIBODY: MATERIAL TO BE DETECTED | RELATIVE VALUE | | | |
| 1 | Material a | 3.80E-10 | 2.60E-11 | 38 | (1, 1) | 2 | 15 |
| 2 | Material b | 5.60E-10 | 8.80E-11 | 56 | (2, 1) | 1 | 20 |
| 3 | Material c | 1.20E-10 | 4.40E-11 | 12 | (3, 1) | 3 | 40 |

[Fig. 8]
DATA STRUCTURE   SENSOR CHIP []

|  | REMARK |
|---|---|
| NAME_OF_MATERIAL_TO_BE_DETECTED | NAME OF MATERIAL TO BE DETECTED |
| Dtc_Tim | DETECTION PROCESSING TIME FOR EACH SPOT |
| S_Pos | POSITION INFORMATION OF SPOT ON SENSOR CHIP |
| Dtc_AIn | ORDER OF DETECTION PROCESSING |
| Dtc_Val | FLUORESCENCE INTENSITY |
| Dtc_BL | BLANK |
| Dtc_EA | ENHANCEMENT ANGLE |

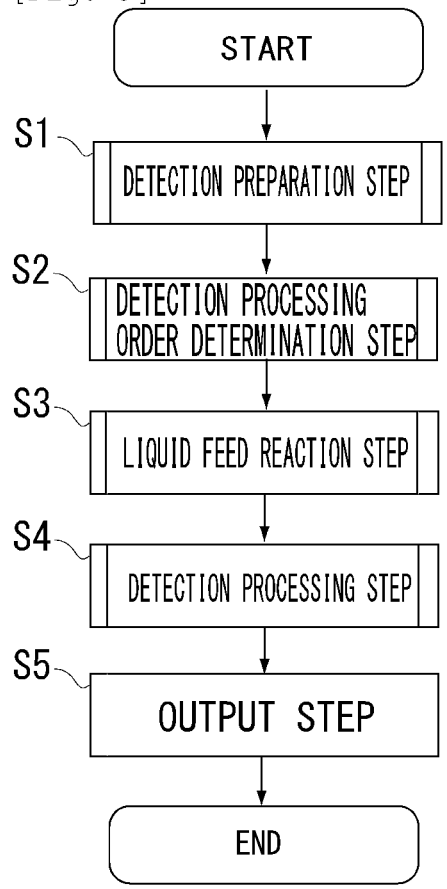

[Fig. 10]
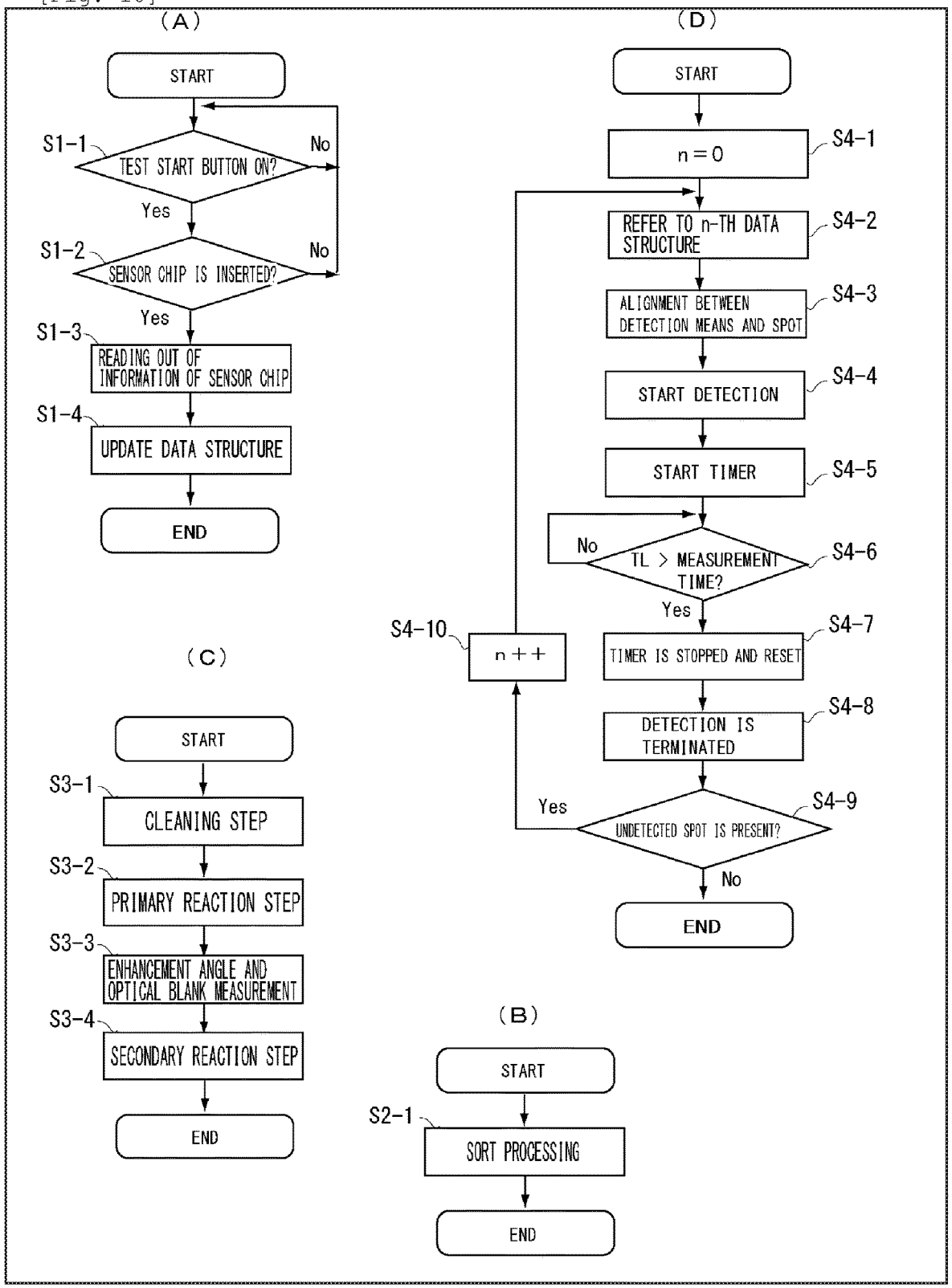

[Fig. 11]
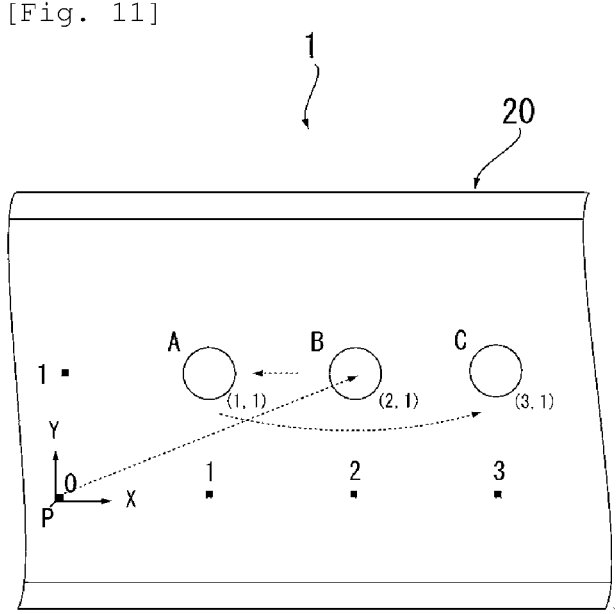

[Fig. 12]

(A) FORE SORTING)

| | SPOT [0] | SPOT [1] | SPOT [2] |
|---|---|---|---|
| NAME OF MATERIAL TO BE DETECTED | MATERIAL a | MATERIAL b | MATERIAL c |
| Dtc_Tim | 15 | 20 | 40 |
| S_Pos | (1, 1) | (2, 1) | (3, 1) |
| Dtc_Aln | 2 | 1 | 3 |
| Rtv_Val | 38 | 56 | 12 |
| Diss_Cst | 3.80E-10 | 5.60E-10 | 1.20E-10 |
| Dtc_Val | | | |
| Dtc_BL | | | |
| Dtc_EA | | | |

(B) DATA STRUCTURE SPOT [] (AFTER SORTING)

| | SPOT [0] | SPOT [1] | SPOT [2] |
|---|---|---|---|
| NAME OF MATERIAL TO BE DETECTED | MATERIAL b | MATERIAL a | MATERIAL c |
| Dtc_Tim | 20 | 15 | 40 |
| S_Pos | (2, 1) | (1, 1) | (3, 1) |
| Dtc_Aln | 1 | 2 | 3 |
| Rtv_Val | 56 | 38 | 12 |
| Diss_Cst | 5.60E-10 | 3.80E-10 | 1.20E-10 |
| Dtc_Val | | | |
| Dtc_BL | | | |
| Dtc_EA | | | |

[Fig. 13]
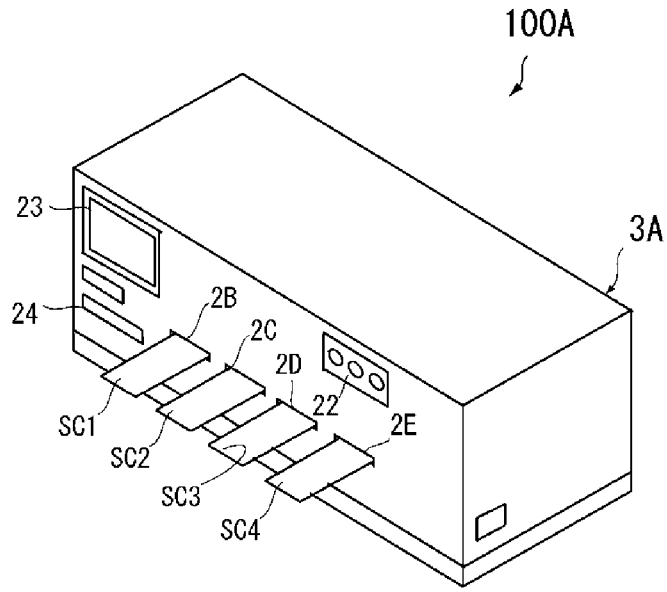
[Fig. 13A]
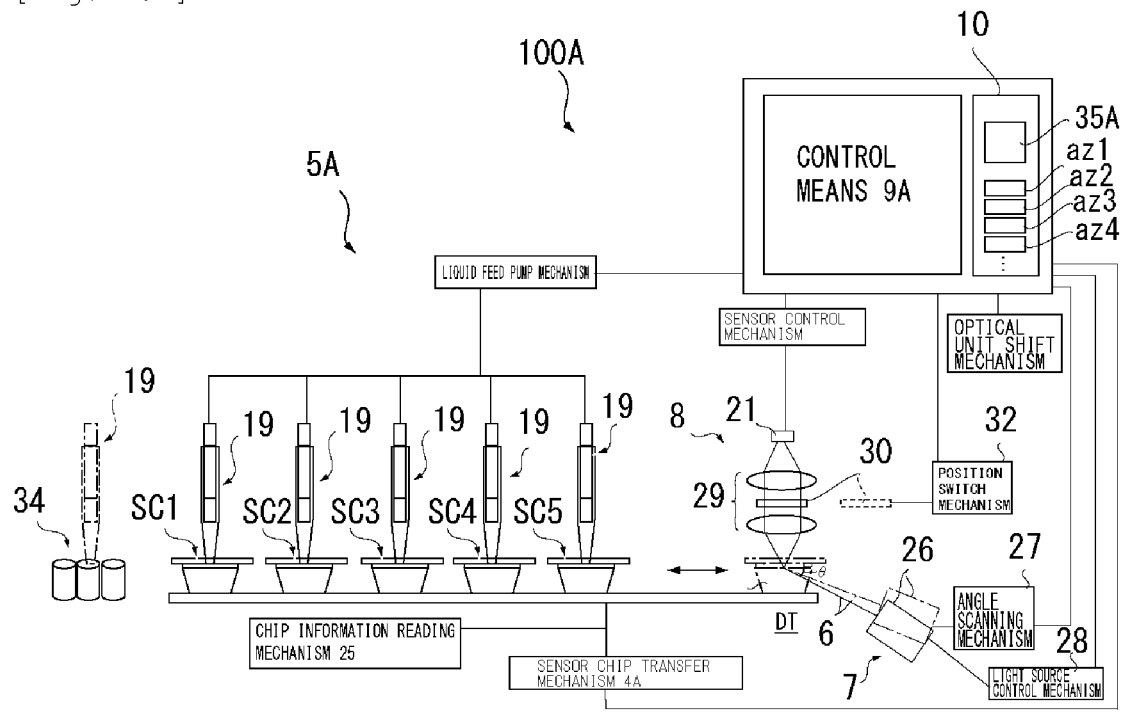

[Fig. 14]

INFORMATION HELD BY SENSOR CHIP SC1

(A)

| SPOT ID | NAME OF MATERIAL TO BE DETECTED | SPOT POSITION | DETECTION MODE | MEASUREMENT TIME (second) |
|---|---|---|---|---|
| 1 | MATERIAL d | (1, 1) | 1 | 10 |
| 2 | MATERIAL e | (1, 2) | | 15 |
| 3 | MATERIAL f | (2, 1) | | 20 |
| 4 | MATERIAL g | (2, 2) | | 10 |

INFORMATION HELD BY SENSOR CHIP SC2

(B)

| SPOT ID | NAME OF MATERIAL TO BE DETECTED | SPOT POSITION | DETECTION MODE | MEASUREMENT TIME (SECOND) |
|---|---|---|---|---|
| 1 | MATERIAL d | (1, 1) | 2 | 10 |
| 2 | MATERIAL e | (1, 2) | | 15 |
| 3 | MATERIAL f | (2, 1) | | 20 |
| 4 | MATERIAL g | (2, 2) | | 10 |

INFORMATION HELD BY SENSOR CHIP SC3

(C)

| SPOT ID | NAME OF MATERIAL TO BE DETECTED | SPOT POSITION | DETECTION MODE | MEASUREMENT TIME (SECOND) |
|---|---|---|---|---|
| 1 | MATERIAL d | (1, 1) | 3 | 10 |
| 2 | MATERIAL e | (1, 2) | | 15 |
| 3 | MATERIAL f | (2, 1) | | 20 |
| 4 | MATERIAL g | (2, 2) | | 10 |

INFORMATION HELD BY SENSOR CHIP SC4

(D)

| SPOT ID | NAME OF MATERIAL TO BE DETECTED | SPOT POSITION | DETECTION MODE | MEASUREMENT TIME (SECOND) |
|---|---|---|---|---|
| 1 | MATERIAL d | (1, 1) | – | 10 |
| 2 | MATERIAL e | (1, 2) | | 15 |
| 3 | MATERIAL f | (2, 1) | | 20 |
| 4 | MATERIAL g | (2, 2) | | 10 |

[Fig. 15]

DATA STRUCTURE    SENSOR CHIP

| | REMARK |
|---|---|
| NAME OF MATERIAL TO BE DETECTED | NAME OF MATERIAL TO BE DETECTED |
| Dtc_Tim | DETECTION PROCESSING TIME FOR EACH SPOT |
| S_Pos | INFORMATION OF SPOT POSITION ON SENSOR CHIP |
| Dtc_Mode | DETECTION MODE |
| Dtc_Pri | PRIORITY OF DETECTION PROCESSING |
| Dtc_Val | FLUORESCENCE INTENSITY |
| Dtc_BL | BLANK VALUE |
| Dtc_EA | ENHANCEMENT ANGLE |

[Fig. 16]

| MODE | DATABASE | REMARK |
|---|---|---|
| 1 | az1 | DETECTION PROCESSING IN DESCENDING ORDER OF DISSOCIATION CONSTANT |
| 2 | az2 | DETECTION PROCESSING IN ASCENDING ORDER OF DETECTION THRESHOLD |
| 3 | az3 | DETECTION PROCESSING IN DESCENDING ORDER OF REQUIRED QUANTITATIVITY |
| null | – | DETECTION PROCESSING IN ORDER IN WHICH TIME OF DETECTION OPERATION OF DEVICE IS SHORTEST |

[Fig. 17]

| ORDER | NAME OF MATERIAL TO BE DETECTED | DISSOCIATION CONSTANT (mol/L) | | |
|---|---|---|---|---|
| | | CAPTURE ANTIBODY: MATERIAL TO BE DETECTED | LABELED ANTIBODY: MATERIAL TO BE DETECTED | RELATIVE VALUE |
| 1 | MATERIAL b | 5.60E-10 | 8.80E-11 | 56 |
| 2 | MATERIAL f | 4.40E-10 | 1.20E-10 | 44 |
| 3 | MATERIAL a | 3.80E-10 | 2.60E-11 | 38 |
| 4 | MATERIAL d | 2.20E-10 | 8.80E-12 | 22 |
| 5 | MATERIAL c | 1.20E-10 | 4.40E-11 | 12 |
| 6 | MATERIAL e | 6.80E-11 | 9.50E-11 | 9 |
| 7 | MATERIAL g | 8.00E-11 | 6.60E-11 | 8 |

[Fig. 18]

| ORDER | NAME OF MATERIAL TO BE DETECTED | DETECTION THRESHOLD (ng/mL) |
|---|---|---|
| 1 | MATERIAL b | 2 |
| 2 | MATERIAL d | 5 |
| 3 | MATERIAL c | 10 |
| 4 | MATERIAL f | 12 |
| 5 | MATERIAL a | 20 |
| 6 | MATERIAL g | 50 |
| 7 | MATERIAL e | 100 |

[Fig. 19]

| ORDER | NAME OF MATERIAL TO BE DETECTED | QUANTITATIVITY (±%) |
|---|---|---|
| 1 | MATERIAL c | 8 |
| 2 | MATERIAL a | 10 |
| 3 | MATERIAL f | 12 |
| 4 | MATERIAL d | 15 |
| 5 | MATERIAL b | 20 |
| 6 | MATERIAL e | 50 |
| 7 | MATERIAL g | 100 |

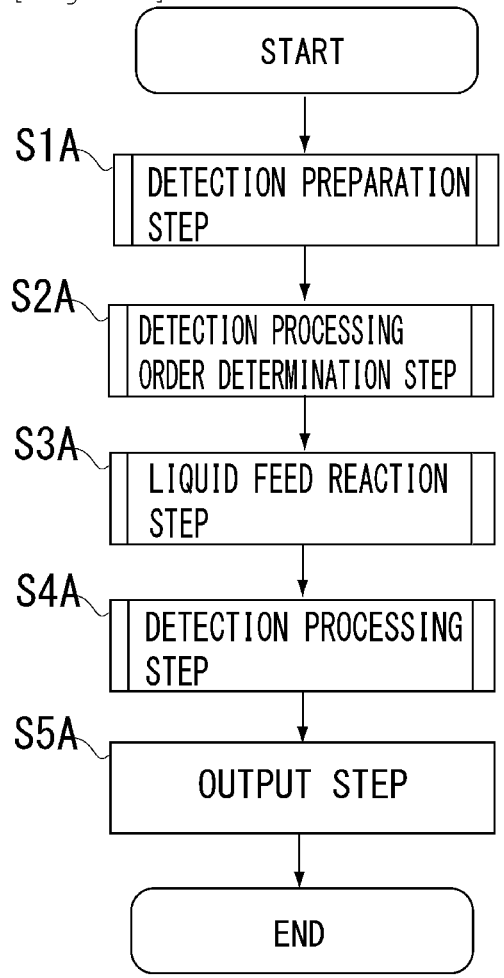
[Fig. 20]

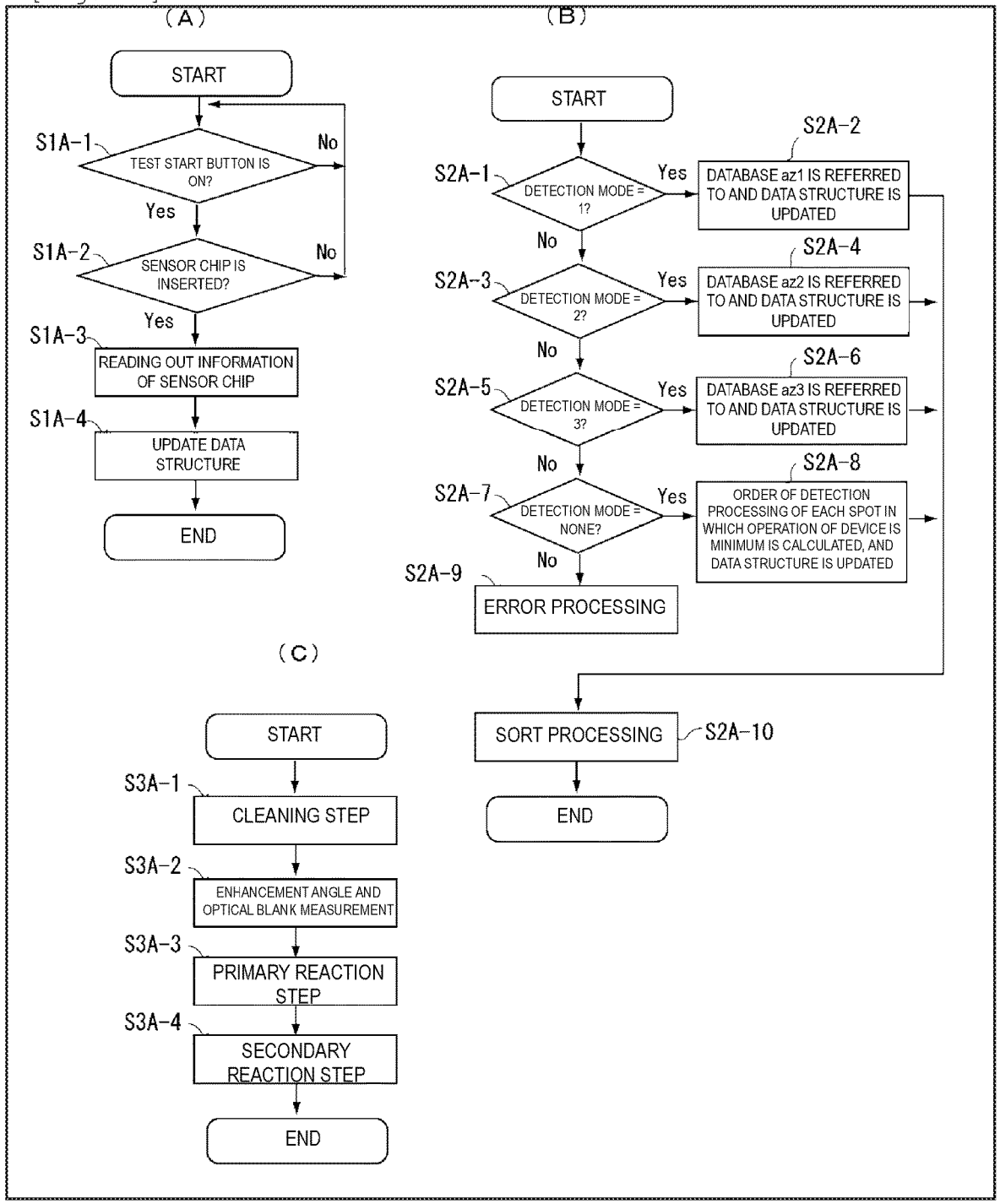

[Fig. 22]
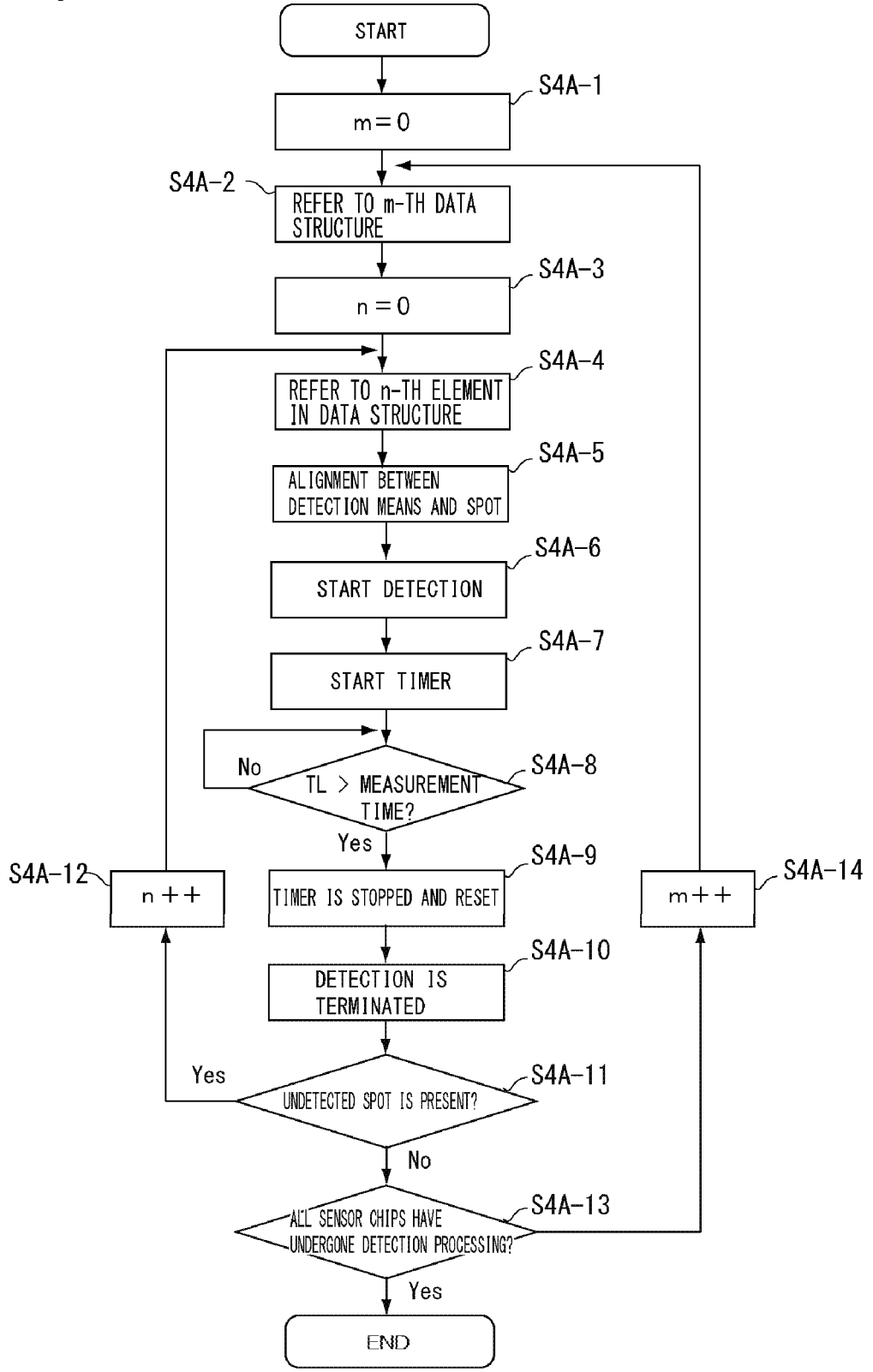

[Fig. 23]

(A) DATA STRUCTURE   SC1_SPOT [ ] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 1 | 1 | 1 | 1 |
| Dtc_Pri | | | | |
| Dtc_Val | | | | |
| Dtc_BL | | | | |
| Dtc_EA | | | | |

(B) DATA STRUCTURE   SC1_SPOT [ ] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 1 | 1 | 1 | 1 |
| Dtc_Pri | 4 | 6 | 7 | 2 |
| Dtc_Val | | | | |
| Dtc_BL | | | | |
| Dtc_EA | | | | |

(C) DATA STRUCTURE   SC1_SPOT [ ] (AFTER SORTING)

| | SPOT [0] | SPOT [1] | SPOT [2] | SPOT [3] |
|---|---|---|---|---|
| NAME OF MATERIAL TO BE DETECTED | MATERIAL f | MATERIAL d | MATERIAL e | MATERIAL g |
| Dtc_Tim | 10 | 10 | 15 | 20 |
| S_Pos | (2, 2) | (1, 1) | (1, 2) | (2, 1) |
| Dtc_Mode | 1 | 1 | 1 | 1 |
| Dtc_Pri | 2 | 4 | 6 | 7 |
| Dtc_Val | | | | |
| Dtc_BL | ... | ... | ... | ... |
| Dtc_EA | ... | ... | ... | ... |

[Fig. 24]

(A) DATA STRUCTURE   SC2_SPOT [] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 2 | 2 | 2 | 2 |
| Dtc_Pri | | | | |
| Dtc_Val | | | | |
| Dtc_BL | | | | |
| Dtc_EA | | | | |

(B) DATA STRUCTURE   SC2_SPOT [] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 2 | 2 | 2 | 2 |
| Dtc_Pri | 2 | 7 | 6 | 4 |
| Dtc_Val | | | | |
| Dtc_BL | | | | |
| Dtc_EA | | | | |

(C) DATA STRUCTURE   SC2_SPOT [] (AFTER SORTING)

| | SPOT[0] | SPOT[1] | SPOT[2] | SPOT[3] |
|---|---|---|---|---|
| NAME OF MATERIAL TO BE DETECTED | MATERIAL d | MATERIAL f | MATERIAL g | MATERIAL e |
| Dtc_Tim | 10 | 10 | 20 | 15 |
| S_Pos | (1, 1) | (2, 2) | (2, 1) | (1, 2) |
| Dtc_Mode | 2 | 2 | 2 | 2 |
| Dtc_Pri | 2 | 4 | 6 | 7 |
| Dtc_Val | | | | |
| Dtc_BL | | ... | ... | ... | ... |
| Dtc_EA | | ... | ... | ... | ... |

[Fig. 25]

(A) DATA STRUCTURE SC3_SPOT [] (BEFORE SORTING)

|  | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 3 | 3 | 3 | 3 |
| Dtc_Pri |  |  |  |  |
| Dtc_Val |  |  |  |  |
| Dtc_BL |  |  |  |  |
| Dtc_EA |  |  |  |  |

(B) DATA STRUCTURE SC3_SPOT [] (BEFORE SORTING)

|  | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | 3 | 3 | 3 | 3 |
| Dtc_Pri | 4 | 6 | 7 | 3 |
| Dtc_Val |  |  |  |  |
| Dtc_BL |  |  |  |  |
| Dtc_EA |  |  |  |  |

(C) DATA STRUCTURE SC3_SPOT [] (AFTER SORTING)

|  | SPOT [0] | SPOT [1] | SPOT [2] | SPOT [3] |
|---|---|---|---|---|
| NAME OF MATERIAL TO BE DETECTED | MATERIAL f | MATERIAL d | MATERIAL e | MATERIAL g |
| Dtc_Tim | 10 | 10 | 15 | 20 |
| S_Pos | (2, 2) | (1, 1) | (1, 2) | (2, 1) |
| Dtc_Mode | 3 | 3 | 3 | 3 |
| Dtc_Pri | 3 | 4 | 6 | 7 |
| Dtc_Val |  |  |  |  |
| Dtc_BL | ... | ... | ... | ... |
| Dtc_EA | ... | ... | ... | ... |

[Fig. 26]

(A) DATA STRUCTURE  SC4_SPOT [] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | – | – | – | – |
| Dtc_Pri | | | | |
| Dtc_Val | | | | |
| Dtc_BL | | | | |
| Dtc_EA | | | | |

(B) DATA STRUCTURE  SC4_SPOT [] (BEFORE SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL g | MATERIAL f |
| Dtc_Tim | 10 | 15 | 20 | 10 |
| S_Pos | (1, 1) | (1, 2) | (2, 1) | (2, 2) |
| Dtc_Mode | – | – | – | – |
| Dtc_Pri | 1(1) | 2(4) | 4(2) | 3(3) |
| Dtc_Val | | | | |
| Dtc_BL | | | | |
| Dtc_EA | | | | |

(C-1) DATA STRUCTURE  SC4_SPOT [] (AFTER SORTING)

| | SPOT [0] | SPOT [1] | SPOT [2] | SPOT [3] |
|---|---|---|---|---|
| NAME OF MATERIAL TO BE DETECTED | MATERIAL d | MATERIAL e | MATERIAL f | MATERIAL g |
| Dtc_Tim | 10 | 15 | 10 | 20 |
| S_Pos | (1, 1) | (1, 2) | (2, 2) | (2, 1) |
| Dtc_Mode | – | – | – | – |
| Dtc_Pri | 1 | 2 | 3 | 4 |
| Dtc_Val | | | | |
| Dtc_BL | ... | ... | ... | ... |
| Dtc_EA | ... | ... | ... | ... |

(C-2) DATA STRUCTURE  SC4_SPOT [] (AFTER SORTING)

| | SPOT [0] | SPOT [1] | SPOT [2] | SPOT [3] |
|---|---|---|---|---|
| NAME OF MATERIAL TO BE DETECTED | MATERIAL d | MATERIAL g | MATERIAL f | MATERIAL e |
| Dtc_Tim | 10 | 20 | 10 | 15 |
| S_Pos | (1, 1) | (2, 1) | (2, 2) | (1, 2) |
| Dtc_Mode | – | – | – | – |
| Dtc_Pri | 1 | 2 | 3 | 4 |
| Dtc_Val | | | | |
| Dtc_BL | ... | ... | ... | ... |
| Dtc_EA | ... | ... | ... | ... |

[Fig. 27]
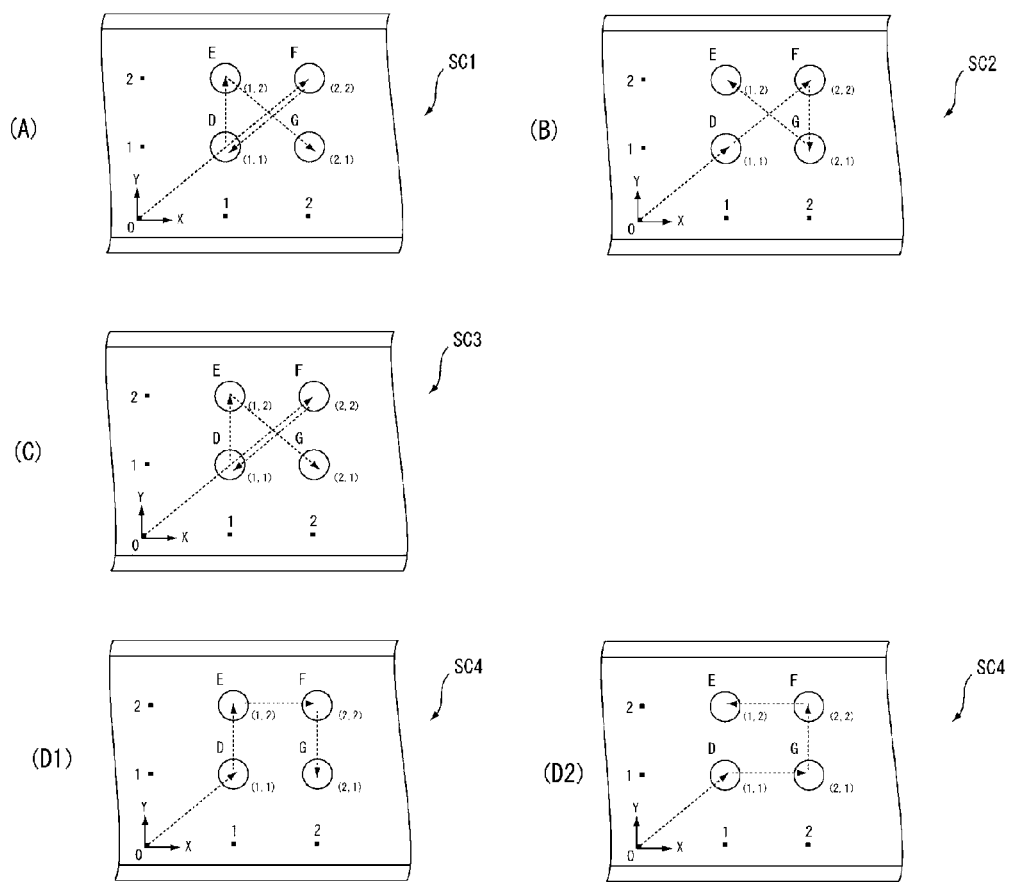

IMMUNOASSAY METHOD AND IMMUNOASSAY SYSTEM

TECHNICAL FIELD

The present invention relates to an immunoassay method and an immunoassay system which can detect a weak light more quickly and with a good quantitativity. More particularly, the present invention relates to an immunoassay method and an immunoassay system in which a specimen contained in a specimen solution is detected, for example, by using surface plasmon resonance (SPR).

BACKGROUND ART

Conventionally, as an immunoassay device which can detect a material to be detected present in a specimen solution with high sensitivity, a device (SPFS device) for a surface plasmon-field enhanced fluorescence spectroscopy (SPFS) using SPR is known (for example, Patent Documents 1 and 2).

In an SPFS device of Patent Document 1, a plurality of metal thin films are provided in an array on a planar portion of a dielectric block (dielectric member) which is used for SPFS; a plurality of capture regions on which a sensing material binding to a specific material (material to be detected) is formed on each of the plurality of metal thin films are formed; a light beam which is emitted from a light source in a state of a divergent light is parallelized; and a plurality of capture regions each of which is in contact with a sample is irradiated with the parallel light simultaneously, whereby a large number of materials to be detected can be analyzed in tandem with each other.

In an SPFS device of Patent Document 1, however, since detection processings are performed simultaneously for a plurality of sensing regions, detection sensitivity becomes lower than those in cases in which a detection processing is individually performed for one sensing region, which is problematic. Since sensing regions are adjacent with each other, there is a problem of an influence by a crosstalk due to adjacent sensing regions. Therefore, like the SPFS device of Patent Document 1, a plurality of sensing regions are simultaneously detected, the detection cannot be performed with high sensitivity, which is problematic.

On the other hand, Patent Document 2 relates to a sensor chip for SPFS having a dielectric member, in which each of a plurality of capture regions for detecting a material to be detected is formed such that shortest distances from a plane of incidence of the dielectric member are the same, thereby minimizing unevenness in measurement data of a fluorescence signal between a plurality of capture regions and improving measurement accuracy.

Since the SPFS device of Patent Document 2 is a device which performs a detection processing by shifting a projector (light source) with respect to each of a plurality of capture regions to individually irradiate a plurality of capture regions, detection is possible with a higher sensitivity than a device in which detection processings are simultaneously performed with respect to a plurality of capture regions as in Patent Document 1. With the SPFS device of Patent Document 2, however, the order of a plurality of capture regions on each of which a detection processing is performed is not determined, and in addition, transition of a detection processing action from one capture region to another capture region takes some amount of time, and therefore, a detection processing is not performed in the order matching a purpose of detection such as a purpose of detecting with high accuracy, whereby a detection result which should naturally be obtained is not obtained, which is problematic.

PRIOR ART REFERENCE

Patent Document

[Patent Document 1] Japanese Unexamined Patent Application Publication No. 2004-239715
[Patent Document 2] WO2012/090759

SUMMARY OF THE INVENTION

Problems to be Solved by the Invention

The present invention has been made in view of the above-described problems, and aims at providing an immunoassay method and an immunoassay system in which a detection processing is performed in the order matching a purpose of detection and an appropriate detection result such as a highly sensitive detection can be obtained.

Technical Solution

An immunoassay method on which one aspect of the present invention is reflected in order to realize at least one of the above-described objects is an immunoassay method in which, by using a sensor chip on which a plurality of capture regions which capture a material to be detected by a first capturing body are arranged separated from each other, the material to be detected captured by the first capturing body is individually detected, wherein the plurality of capture regions are formed by using a different type of first capturing body depending on the type of a material to be detected to be captured, the method comprising: a detection processing order determination step of determining a detection processing order between the capture regions based on information about a detection processing order between the plurality of the capture regions; and a detection processing step of performing a detection processing for each of the capture regions according to the detection processing order between the plurality of the capture regions.

An immunoassay system on which one aspect of the present invention is reflected in order to realize at least one of the above-described objects is an immunoassay system at least comprising:

a sensor chip comprising a plurality of capture regions on which a first capturing body capturing a material to be detected is immobilized separated from each other; and optical detection means by which the plurality of capture regions are scanned to detect the material to be detected by detecting a fluorescence signal obtained by excitation of a fluorescent material with which the material to be detected is labeled, which is provided with an information storage medium storing information about a detection processing order, and which has detection processing order determination means in which the information about the detection processing order stored in the information storage medium is processed to determine the detection processing order.

Advantageous Effects of Invention

According to the present invention, an immunoassay method and an immunoassay system in which a detection processing is performed for a plurality of capture regions in an optimal order matching a purpose of detection and an appropriate detection result is obtained are provided.

BRIEF DESCRIPTION OF DRAWINGS

FIG. 1 is a diagram illustrating an outer appearance of an immunoassay device of a first embodiment.

FIG. 2 is a schematic diagram illustrating an internal structure of the immunoassay device of FIG. 1.

FIG. 3 is a block diagram illustrating an overall configuration of an immunoassay system including the immunoassay device of FIG. 1.

FIG. 4 is an exploded perspective diagram illustrating a sensor chip to be inserted in the immunoassay device of FIG. 1.

FIG. 5 illustrates a cross-sectional view of the sensor chip illustrated in FIG. 4.

FIG. 6 is a diagram illustrating a state in which an optical detection is performed on a sensor unit by using the immunoassay device of FIG. 1.

FIG. 7 is a diagram partially illustrates information of a sensor chip including in a bar code of the sensor chip of FIG. 4.

FIG. 8 is a diagram describing a data structure used in the immunoassay method of the first embodiment.

FIG. 9 is a diagram illustrating a main flow of the immunoassay method by the immunoassay device of the first embodiment.

FIG. 10 is a diagram illustrating a sub-flow of each step of the immunoassay method of FIG. 9. (A) is a diagram illustrating a sub-flow of a detection preparation step of FIG. 9. (B) is a diagram illustrating a sub-flow of a detection processing order determination step of FIG. 9. (C) is a diagram illustrating a sub-flow of a liquid feed reaction step of FIG. 9. (D) is a diagram illustrating a sub-flow of a detection processing step of FIG. 9.

FIG. 11 is a diagram illustrating an arrangement of each capture region fixed on a sensor unit on the surface of a sensor chip of the first embodiment, and an order of detection processing of each capture region.

FIG. 12(A) is a diagram illustrating a state in which information of the sensor chip of FIG. 7 is stored in the data structure of FIG. 8. (B) is a diagram illustrating a state in which the data structure of (A) was sorted in ascending order of detection processing order (Dtc_Aln).

FIG. 13 is a diagram illustrating an outer appearance of an immunoassay device of a second embodiment.

FIG. 13A is a block diagram illustrating an overall configuration of an immunoassay system including the immunoassay device of the second embodiment.

FIGS. 14(A) to (D) are diagrams illustrating information held by each sensor chip.

FIG. 15 is a diagram describing a data structure used for the immunoassay method of the second embodiment.

FIG. 16 is a diagram illustrating a name of database and its description referred to for each detection mode.

FIG. 17 is a diagram illustrating the contents of a database referred to when the detection mode is "1".

FIG. 18 is a diagram illustrating the contents of a database referred to when the detection mode is "2".

FIG. 19 is a diagram illustrating the contents of a database referred to when the detection mode is "3".

FIG. 20 is a diagram illustrating a main flow of an immunoassay method by the immunoassay device of the second embodiment.

FIG. 21 is a diagram illustrating a sub-flow of each step of the immunoassay method of FIG. 20. (A) is a diagram illustrating a sub-flow of the detection preparation step of FIG. 20. (B) is a diagram illustrating a sub-flow of the detection processing order determination step of FIG. 20. (C) is a diagram illustrating a sub-flow of a liquid feed reaction step of FIG. 20.

FIG. 22 is a diagram illustrating a sub-flow of the detection processing step of FIG. 20.

FIGS. 23(A) to (C) are diagrams illustrating a transition of a data structure when a detection processing order determination step is performed on a sensor chip in mode 1 (see FIG. 16).

FIGS. 24(A) to (C) are diagrams illustrating a transition of a data structure when a detection processing order determination step is performed on a sensor chip in mode 2 (see FIG. 16).

FIGS. 25(A) to (C) are diagrams illustrating a transition of a data structure when a detection processing order determination step is performed on a sensor chip in mode 3 (see FIG. 16).

FIGS. 26(A) to (C-2) are diagrams illustrating a transition of a data structure when a detection processing order determination step is performed on a sensor chip without mode information (null) (see FIG. 16).

FIGS. 27(A) to (C), and (D1) or (D2) are diagrams illustrating states in which detection processings are performed on a plurality of capture regions of each sensor chip in order based on a detection processing order determined for each sensor chip in modes 1 to 3 and in cases without mode information, respectively.

MODE FOR CARRYING OUT THE INVENTION

«First Embodiment»

In the following, an immunoassay method and an immunoassay system of a first embodiment according to the present invention will be described in detail with reference to FIG. 1 to FIG. 12.

The immunoassay system of the first embodiment has a sensor chip 1 and an immunoassay device 100 as illustrated in FIG. 1.

[Immunoassay Device]

The immunoassay device 100 of the first embodiment is an SPFS device which detects a specimen contained in a specimen solution by applying a surface plasmon resonance (SPR) phenomenon.

The immunoassay device 100 has, as illustrated in FIG. 1 to FIG. 6, a casing 3 in which a slot 2A for inserting a sensor chip 1 is formed, a sensor chip transfer mechanism 4 which shifts the sensor chip 1 to a predetermined position, a liquid transfer mechanism 5 which feeds a liquid to the sensor chip 1, a light projection optical system 7 which projects an excitation light 6 to the sensor chip 1 at a detectable position DT (see FIG. 3), a light-receiving optical system 8 which receives a fluorescence emitted from the sensor chip 1 which has received the excitation light 6, control means 9 which controls operations of the above-described mechanisms and optical systems, a storage means 10 used for the control means 9, and the like. In examples illustrated in FIG. 2 and FIG. 3, the light projection optical system 7 and the light-receiving optical system 8 are integrally constituted as an optical unit 36, and the optical unit 36 is shiftably configured by an optical unit shift mechanism 37.

[Sensor Chip]

First, the sensor chip 1 used for the immunoassay device 100 of the present embodiment will be described.

The sensor chip 1 at least has, as illustrated in FIG. 4, a dielectric member 11, an metal thin film 12 formed on the top surface of the dielectric member 11, a micro flow channel component member 13 provided on the metal thin film 12, and an information storage medium 14. By superimposing the micro flow channel component member 13 on the metal thin film 12, a micro flow channel 15 (see FIG. 5) is formed on the top surface of the metal thin film 12 of the dielectric member 11. The symbol 13A designates a cover member which covers the micro flow channel component member 13 or the like.

The dielectric member 11 may be any material as long as it is optically transparent to an excitation light, and is preferably a variety of inorganic substances ($SiO_2$ or the like) or synthetic polymers (PMMA, PC, or the like). A material which generates a small amount of autofluorescence due to irradiation of an excitation light is preferable, and for example, a cycloolefin polymer is preferable.

The shape of the dielectric member 11 is, for example, a pyramid shape, a truncated pyramid shape, or the like such as a hexahedron having nearly a trapezoidal sectional shape (truncated quadrangular pyramid shape), a quadrangular pyramid, a cone, a triangular pyramid, or a polyangular pyramid, which can be formed, for example, by injection molding.

The metal thin film 12 of the sensor chip 1 preferably consists of at least one selected from the group consisting of gold, silver, aluminum, copper, and platinum, and can be formed on the dielectric member 11 by a sputtering method, an evaporation method, an electrolytic plating method, an electroless plating method, or the like.

The thickness of the metal thin film 12 is preferably 5 to 500 nm, and from the viewpoint of an electric field enhancement effect, when the material of the metal thin film 12 is gold, silver, copper, or platinum, the thickness is preferably 20 to 70 nm; when the material is aluminum, the thickness is preferably 10 to 50 nm; and when the material is an alloy of these metals, the thickness is preferably 10 to 70 nm.

As a method of fixing the micro flow channel component member 13 on the metal thin film 12, a method of fixing by using an adhesive, a matching oil, or a transparent adhesive sheet having a same photorefractive index as that of the dielectric member 11 is preferable.

FIG. 5 illustrates a cross section of the sensor chip 1 along a flow channel. In the sensor chip 1, as illustrated in FIG. 5, the micro flow channel 15 is formed on the metal thin film 12 by the micro flow channel component member 13, a liquid discharge/suction unit 16 is provided on the upstream side (on the left in FIG. 5) of the micro flow channel 15, and a liquid mixing unit 17 is provided on the downstream side.

The liquid discharge/suction unit 16 and the liquid mixing unit 17 on the top surface are sealed by a hermetic seal 18 as illustrated in FIG. 5, and are configured such that the hermetic seal 18 on the liquid discharge/suction unit 16 side is broken through by the tip (see FIG. 3) of a liquid feed pump 19, thereby providing the micro flow channel 15 with a liquid (a specimen solution, a cleaning liquid, a fluorescently labeled secondary antibody solution, or the like).

The micro flow channel 15 is provided with a sensor unit 20 for performing an immunoassay reaction, and on the sensor unit 20, a capture antibody (first capturing body) as a primary antibody which specifically binds to specific materials to be detected a to c contained in a specimen solution is immobilized at a plurality of locations as spots (capture regions) A to C in regions separated with each other (see FIG. 5, FIG. 6, and FIG. 11).

FIG. 6 illustrates a perspective diagram of the sensor unit 20, and FIG. 11 illustrates the top surface of the sensor unit 20. In the examples illustrated in FIG. 6 and FIG. 11, capture regions A to C are immobilized linearly in three regions separated with each other.

Each of the capture regions A to C is, as illustrated in FIG. 11, immobilized at a position specified by coordinates in X-axis direction and Y-axis direction relative to a specific base point P(0, 0).

As described below, each position information of each of the capture regions A to C specified by the coordinates of X-axis and Y-axis is used when optical detection means 21 is shifted to a detection position corresponding to each of the capture regions A to C when these capture regions are individually detected by the optical detection means 21 of the light-receiving optical system 8.

Examples of a method of immobilizing each primary antibody as capture regions A to C on the metal thin film 12 include a method in which a SAM (Self-Assembled Monolayer: self-organized monomolecular film) is formed on the surface of the metal thin film 12 by a commercially available SAM-forming reagent (for example, 10-carboxy-1-decane thiol), and then, a solution of a capture antibody as a primary antibody containing N-hydroxy succinic acid imide (NHS) is brought into contact with the SAM to bind the SAM to the capture antibody, thereby immobilizing the capture antibody to the sensor unit 20.

Examples of another method of the immobilization include a method in which a hydrophilic macromolecule is immobilized on a SAM by Schiff's linkage between a reducing terminal of the hydrophilic macromolecule such as carboxymethyl dextran (CMD) and an amino group of the SAM, the immobilized portion on a region of the metal thin film 12 is immersed in a 50 mM to 100 mM N-hydroxy succinic acid imide and water-soluble carbodiimide, and then, a solution of a capture antibody is brought into contact with the region to immobilize the capture antibody as a primary antibody on CMD, whereby the capture antibody is immobilized on the metal thin film 12 via the hydrophilic macromolecule and the SAM.

Further, the sensor chip 1 is desirably integrally joined with a chemical well 34 containing a variety of solutions (a specimen solution, a buffer solution, and a cleaning liquid) or the like to be provided into the sensor chip (see FIG. 2, a joint is not illustrated). By integrally joining the chip with the well, only one operation of insertion into an immunoassay device by a user is required.

The information storage medium 14 (see FIG. 4) of the sensor chip 1 stores information (hereinafter, referred to as "an information about the sensor chip 1") about processing of the sensor chip 1.

The information about a sensor chip has, for example, as illustrated in FIG. 7, "a name of a material to be detected" representing the name of a material to be detected to be captured at each capture region of the sensor unit 20, "a spot position" representing coordinates (X, Y) of the center of each of capture regions A to C relative to a base point P(0, 0) on the surface of the micro flow channel 15 of the sensor chip 1, "a measurement order" (information about a detection processing order) representing an order when the larger of a dissociation constant (first dissociation constant) between a capture antibody and a material to be detected and a dissociation constant (second dissociation constant) between a material to be detected and a labeled antibody (second capturing body) is selected for each of capture antibodies immobilized on a sensor chip, and the selected dissociation constants of the capture antibodies are arranged in the descending order, "a measurement time" representing a time which should be consumed for detection when a processing (hereinafter, simply referred to as "a detection processing") for detecting a fluorescence from each of capture regions A to C is performed, a first dissociation constant, a second dissociation constant, or the like. All of these pieces of information need not be included, and at least, information required for determining a detection processing order may be included. Materials a to c of the material to be detected represent materials to be captured by capture antibodies of the capture regions A to C.

The information storage medium 14 is preferably, for example, as illustrated in FIG. 4, configured to be provided on the surface of the hermetic seal 18 of the sensor chip 1 such that information of the sensor chip 1 is read out by the immunoassay device 100 at the same time when the sensor chip 1 is inserted into a slot 2A of the immunoassay device 100.

Since the information storage medium 14 only has to have information of the sensor chip 1, a bar code, a hologram, a character, a symbol, a two-dimensional bar code, an IC chip, or the like can be used as the information storage medium 14. Further, by forming a predetermined notch on a part of the sensor chip 1, the part of the sensor chip 1 may be used as the information storage medium 14 displaying information of the sensor chip 1.

[Casing]

As illustrated in FIG. 1, the casing 3 of the immunoassay device 100 is provided with chip information reading means (not illustrated) for reading out information of the sensor chip 1, an operation unit 22 having input means (operation button or the like) for performing a predetermined operation to input information by a user, a display unit 23 for displaying information to a user, a print output unit 24 for outputting an analysis result, or the like. A user can perform a variety of operations such as a start processing of an immunoassay reaction, an output processing (display processing or print processing) of analysis result by an immunoassay reaction, and confirmation or edit (change in a value or the like) of information of the sensor chip 1 read out from the sensor chip 1, by operating a button of the operation unit 22 while confirming the display unit 23.

On the casing 3 of the immunoassay device 100, as described above, the slot 2A for inserting the sensor chip 1 is formed. The casing 3 is provided with known detection means which, for example, optically detects or mechanically detects whether the sensor chip 1 is inserted into the slot 2A or not, which continues notifying the control means 9 of information representing whether the detection means is inserted or not.

[Chip Information Reading Means]

Chip information reading means (partly not illustrated) is means which reads out information of the sensor chip 1 and transmits the information to the control means 9, and is composed of a chip information reading mechanism 25 and a part of the control means 9.

For the chip information reading mechanism 25, known means can be used, and selected depending on the information storage medium 14 of the sensor chip 1. The chip information reading mechanism 25 (see FIG. 3) is, for example, a bar code reader which reads out chip information from the bar code when the information storage medium 14 is a bar code.

When the information storage medium 14 is provided on the surface of the hermetic seal 18 of the sensor chip 1, desirably, an image sensor or an IC chip reader (not illustrated) is configured to be provided inside the casing 3 in the vicinity of the slot 2A as the chip information reading mechanism 25 to read out information of the sensor chip 1.

[Light Projection Optical System]

The light projection optical system 7 is, similarly to a conventional SPFS device, provided with, for example, as illustrated in FIG. 3, a light source 26, an angle scanning mechanism 27 which adjusts an irradiation angle of the light source 26, a light source control mechanism 28 which controls the light source 26 to adjust the intensity or the like of the excitation light 6 emitted from the light source 26, or the like.

The light projection optical system 7 has a function in which the plane of incidence of the dielectric member 11 constituting the sensor chip 1 which has been transferred to a predetermined detectable position DT by the sensor chip transfer mechanism 4 is irradiated with the excitation light 6 such that a backside portion of the metal thin film 12 having the sensor unit 20 on the top surface at a predetermined incident angle θ which is a total reflection condition is irradiated with the excitation light 6 which has passed through the inside of the dielectric member 11, generating an evanescent wave from the surface of the metal thin film 12, whereby a fluorescent material present in the sensor unit 20 of the sensor chip 1 is excited.

The above-described light source 26 is, for example, a single-mode laser, which emits only P wave with respect to the metal thin film 12 toward a plane of incidence of a prism. By using a laser diode (hereinafter, referred to as "an LD") as the light source 26, a light is introduced to the dielectric member 11 of the sensor chip 1. The light projection optical system 7 is composed of, for example, an LD, a beam forming optical system, an optical filter, an APC mechanism, a temperature control mechanism, or the like (partly not illustrated).

[Light-Receiving Optical System]

The light-receiving optical system 8 is an optical system having the same configuration as that of a conventional SPFS device, and has, for example, as illustrated in FIG. 3, an optical lens group 29, an excitation light cut filter 30 for cutting a component of the excitation light 6, the optical detection means 21 which receives and detects a fluorescence, a sensor control mechanism 31 which controls the operation of the optical detection means 21, a position switch mechanism 32 which positions the excitation light cut filter 30 to an optical axis of the optical lens group 29 or evacuates the excitation light cut filter 30 from the optical axis, and the like.

[Sensor Chip Transfer Mechanism]

The sensor chip transfer mechanism 4 (see FIG. 3) is known means which shifts the sensor chip 1 which has been inserted into the slot 2A to a predetermined position by the control of the control means 9.

The sensor chip transfer mechanism 4, as illustrated in FIG. 2 and FIG. 3, for example, shifts the sensor chip 1 to a predetermined position where a liquid can be fed or shifts the sensor chip 1 which has finished an immunoassay reaction to a detectable position DT.

The sensor chip transfer mechanism 4 has a function of adjusting a relative position of the sensor chip 1 with respect to the optical detection means 21 in accordance with a command of the control means 9. For example, the sensor chip transfer mechanism 4 operates cooperatively with the optical unit shift mechanism 37, and relatively shifts the sensor chip 1 and the optical detection means 21 such that each of the capture regions A to C of the sensor unit 20 of the sensor chip 1 is at a predetermined position where a light can be detected.

[Liquid Transfer Mechanism]

The liquid transfer mechanism 5 has, as illustrated in FIG. 2 and FIG. 3, the liquid feed pump 19 as liquid sending means and a liquid feed pump drive mechanism 33 which drives the liquid feed pump 19, or the like.

The liquid feed pump 19 is shiftably provided inside the casing 3 of the immunoassay device 100, and has, as illustrated in FIG. 3, a function in which various liquids such as a specimen solution, a buffer solution, and a cleaning liquid are collected from the chemical well 34 arranged on a transfer stage to feed a liquid to the sensor chip 1.

[Control Means]

The control means 9 is a general personal computer or the like, which is connected to the above-described sensor chip transfer mechanism 4, liquid transfer mechanism 5, light projection optical system 7, light-receiving optical system 8, and each unit of the casing 3 (the operation unit 22, the display unit 23, the print output unit 24, and the like), or the like, and has a function of controlling these.

The control means 9 has the storage means 10, and the storage means 10 stores the control program 35 (including those illustrated in FIG. 9 and FIG. 10) for performing an immunoassay method according to the present invention, the information about a detection processing order referred to based on chip information read out by the chip information reading mechanism 25, and the like.

The control means 9 functions as each means (including detection processing order determination means) executing a detection preparation step S1, a detection processing order determination step S2, a liquid feed reaction step S3, a detection processing step S4, and an output step S5 as a part of the control program 35. The control program 35 has, as illustrated in FIG. 8, a data structure for dealing with each item data of the information of the sensor chip 1.

The data structure is constituted as what is called in a general program an array of a structure, which is, as illustrated in FIG. 8, for storing information of the sensor chip 1 which has been inserted into the immunoassay device 100.

The data structure at least has "a name of a material to be detected" representing a name of a material to be detected captured by each of the capture regions A to C of the sensor unit 20 of the sensor chip 1, "S_Pos" for storing position information of the capture regions A to C, and "Dtc_Aln" for storing information representing the order of detection processings of the capture regions A to C.

The "Dtc_Tim" stores a time which should be consumed for detection of a fluorescence from a capture region; the "Dtc_Val" stores a value of a fluorescence intensity measured by the detection; the "Dtc_BL" stores a value of an optical blank at a capture region position; and the "Dtc_EA" is a property for storing an enhancement angle in a capture region.

<Immunoassay Method>

In the following, examples in which an immunoassay method is performed by using the immunoassay device 100 of the first embodiment will be described with reference to FIG. 9 to FIG. 12.

[Detection Preparation Step]

In a step S1-1 of the detection preparation step S1 (see FIG. 9), as illustrated in FIG. 10(A), whether the operation unit 22 in the casing 3 of the immunoassay device 100 is operated by a user to switch a test start button to ON or not is determined. When the determination is YES, the process proceeds to a step S1-2, and when the determination is No, the process returns to the step S1-1.

In the step S1-2, the control means 9 determines whether the sensor chip 1 is inserted into the slot 2A by the operation of a user or not based on information from detection means. When the sensor chip 1 is inserted and the determination is YES, the process proceeds to a step S1-3, and when the sensor chip 1 is not inserted into the slot 2A and the determination is NO, the process returns to the step S1-1.

In the step S1-3, the control means 9 reads out information of the sensor chip 1 from the sensor chip 1 which has been inserted into the slot 2A.

In the step S1-4, data (see FIG. 7) relating to each of the capture regions A to C of the read out information of the sensor chip 1 is stored as an array element of the data structure of FIG. 8. A state after storing the data is illustrated in FIG. 12(A).

[Detection Processing Order Determination Step]

In a step S2-1 (see FIG. 10(B)) of the detection processing order determination step S2 (see FIG. 9), the control means 9 sorts an array of the data structure in ascending order of the detection processing order (Dtc_Aln) (see FIGS. 12(A) and (B) comparing to each other). The sorting processing may be a sorting processing in descending order of a value of the relative value or dissociation constant, by using information (Rtv_val) of a relative value of a dissociation constant as illustrated in FIG. 7 or information of a value (Diss_cst) itself of a dissociation constant.

By this sort processing, as illustrated in FIG. 12(B), an order (detection processing order) in which detection processing of each capture region is performed (detection processing order) is determined. In an example illustrated in FIG. 12(B), it is determined that detection processings are performed in the following order of materials to be detected: "material b"→"material a"→"material c".

[Liquid Feed Reaction Step]

In a cleaning step of the step S3-1 (see FIG. 10(C)) of the liquid feed reaction step S3 (see FIG. 9), the sensor chip 1 is shifted to a position where a liquid can be fed (see FIG. 3), a buffer solution is fed by the liquid transfer mechanism 5 to remove a moisturing agent, and then, a processing of feeding a cleaning liquid is performed.

In a step S3-2, a specimen solution is fed to the micro flow channel 15, and a primary reaction in which a material to be detected in the specimen solution is bound to each capture antibody fixed to each of the capture regions A to C of the sensor unit 20 is performed. After that, the sensor chip 1 is shifted to a detectable position DT (see FIG. 3).

In a step S3-3, as illustrated in FIG. 3, the optical detection means 21 is shifted to a detection position of any one of the capture regions A to C of the sensor unit 20, and the excitation light cut filter 30 is evacuated from an optical axis. A plasmon enhancement angle is then measured, and the value is set as an incident angle ($\theta$) which is used when the excitation light 6 is made incident on the metal thin film 12 in a detection processing described below with respect to each of the capture regions (Dtc_EA). After this setting, the evacuated excitation light cut filter 30 is again inserted into an optical axis of the light-receiving optical system 8. The order of setting of the enhancement angle (incident angle ($\theta$)) and the insertion of the excitation light cut filter 30 may be reversed. After the measurement of the plasmon enhancement angle for each capture region, measurement and setting of an optical blank value for each of the capture regions A to C are performed (Dtc_BL). Measurement and setting of an enhancement angle and measurement and setting of an optical blank value may be performed together for each of the capture regions A to C.

In a step S3-4, the sensor chip 1 is again shifted to a position where a liquid can be fed (see FIG. 3), a solution of an antibody labeled with a fluorescent material is fed to the micro flow channel 15, and the antibody labeled with a fluorescent material is bound to a material to be detected captured by each capture antibody of the sensor unit 20. After that, the sensor chip 1 is shifted to a detectable position DT.

[Detection Processing Step]

In a step S4-1 (see FIG. 10(D)) of the detection processing step S4 (see FIG. 9), an integer value n is set to 0.

In a step S4-2, the n-th element of an array of a data structure which has undergone a sort processing of the step S2-1 is referred to. When n=0, spot [0] (FIG. 12(B)) is referred to.

In a step S4-3, an alignment processing between the optical detection means 21 and each capture region is performed based on position information (spot [n] .S_Pos) of each capture region included in the n-th element. For example, when n=0, the optical detection means 21 is relatively aligned to a position of a capture region B based on position information (spot [0] .S_Pos)=(2, 1) of each capture region included in the 0-th element (see FIG. 11).

Here, the alignment may be such that an optical axis of the optical detection means 21 of the optical unit 36 and a capture region which is a target of detection processing are relatively aligned, the relative alignment can be performed by shifting only the sensor chip transfer mechanism 4, by shifting only the optical unit 36 by the optical unit shift mechanism 37, or by shifting both the sensor chip transfer mechanism 4 and the optical unit 36.

In a step S4-4, a detection processing in which a fluorescence from the capture region to which the optical detection means 21 has been relatively aligned is detected is started, and the process proceeds to a step S4-5, in which a timer is started.

In a step S4-6, whether a time (TL) from the start of the timer is longer than a measurement time (spot [n] .Dtc_Tim) of an array element of a data structure which is referred to or not is determined. When the determination is No in which the time is not longer than the measurement time, the process returns to the step S4-6. On the other hand, the determination is Yes in which the time is longer than the measurement time, the detection processing is terminated and the process proceeds to a step S4-7.

In the step S4-7, the timer is stopped and reset. In a step S4-8, a detection processing for a capture region of a processing target is terminated.

In a step S4-9, whether a capture region which has not undergone a detection processing is present or not (whether an array element of the n+1-th data structure is present or not) is determined, and when the determination is Yes in which the capture region is present, the process proceeds to S4-10 in which the integer value n is incremented, and returns to the step S4-2. On the other hand, when the determination is No in which the capture region which has not undergone a detection processing is not present, the process proceeds to an output step of the step S5.

As described above, when the process returns to the step S4-2, a processing similar to the above-described processing is repeated for each capture region until an array element of a structure of a capture region disappears. By this, each capture region in the sensor unit 20 undergoes a detection processing sequentially in ascending order of the number of an array element of the data structure of FIG. 12(B), in other words, in accordance with an order of a detection processing which the sensor chip 1 has.

In a specific example, based on a structure of a capture region after the sort processing of FIG. 12(B), as illustrated in FIG. 11, a detection processing is performed in the following order: a capture region B in which a material to be detected b is to be captured→a capture region A in which a material to be detected a is to be captured→a capture region C in which a material to be detected c is to be captured.

[Output Step]

In the output step S5 (see FIG. 9), an output processing in which the above-described detected result is displayed on the print output unit 24 or the display unit 23 is performed.

In the following, operations and effects of an immunoassay method and an immunoassay system of the first embodiment will be described.

(1) Since the immunoassay method and the immunoassay system have: a detection processing order determination step which determines a detection processing order between the capture regions based on information about a detection processing order between a plurality of each of the capture regions; and a detection processing step in which a detection processing is performed on each of the capture regions in accordance with the determined detection processing order, a plurality of each of the capture regions A to C of the sensor chip 1 in which a material to be detected is captured can be measured in an order optimum for a detection purpose by the information about a detection processing order.

(2) When information about a detection processing order is stored in the information storage medium 14 of the sensor chip 1, information of an order of a detection processing can be physically linked to the sensor chip 1 itself, which eliminates confusion between the information and information of other sensor chips, whereby, when the information needs to be managed for each sensor chip, the management becomes simple.

(3) When the information about a detection processing order is information about a dissociation constant of a material to be detected, a bad influence of dissociation of a material to be detected on a detection result can be reduced to a minimum by performing detection processing on a capture region in descending order of a dissociation constant.

(4) When the information about a detection processing order is information (for example, information other than the dissociation constant or in addition to information about the dissociation constant, information that a detection processing should be performed in the order of weakness to a specific environment condition such as a temperature of a material to be detected) about the type of a material to be detected, a capture region in which such a material to be detected is captured undergoes a detection processing early, and therefore, a bad influence of a degradation of a material to be detected or the like due to an environmental condition such as a temperature on a detection result can be reduced.

(5) When the information about a detection processing order is information in which the detection processing order is determined in advance, a detection processing is performed preferentially on a specific material to be detected which a user desires, which is advantageous.

(6) When capturing of a material to be detected by a capture antibody (first capturing body) as a primary antibody and fluorescent labeling of the material to be detected by a labeled antibody (second capturing body) which is labeled with a fluorescent material are simultaneously performed in a plurality of capture regions, a reaction can be performed simultaneously in a plurality of capture regions with one liquid feed system, and therefore a detection processing can be performed with low cost and quickly, which is advantageous. In the case of a sensor chip on the premise that a material to be detected is simultaneously captured in a plurality of capture regions, while one capture region undergoes a detection processing, a material to be detected which is captured in another capture region is dissociated over time or the like, and therefore, the above-described effects (1), (3), (4), and (5) of the present invention are particularly effective.

The immunoassay method of the first embodiment is a method in which an order (order of measurement) of detection processing is determined by performing a sorting processing of information in descending order of a dissociation constant of a capture region and a detection processing is performed in accordance with the order. The order is, however, not limited thereto, and a detection processing may be performed as described above in descending order (in ascending order of measurement value) of sensitivity due to a low blood concentration of a material to be detected to be captured by a primary antibody, or in descending order (in descending order of required quantitativity) of accuracy of concentration detection of a material whose concentration is desired to be detected as accurately as possible.

«Second Embodiment»

In the following, an immunoassay method and an immunoassay system of a second embodiment according to the present invention will be described in detail with reference to FIG. 13 to FIG. 27.

The immunoassay system of the second embodiment has sensor chips SC1 to SC4 and an immunoassay device 100A.

[Immunoassay Device]

The immunoassay device 100A of the second embodiment is a surface plasmon-field enhanced fluorescence spectroscopy device (SPFS device) in which a specimen contained in a specimen solution is detected by applying a Surface Plasmon Resonance (SPR) phenomenon.

The immunoassay device 100A has, as illustrated in FIG. 13 and FIG. 13A, a casing 3A in which slots 2B to 2E for inserting sensor chips SC1 to SC4 are formed, a sensor chip transfer mechanism 4A which shifts the sensor chips SC1 to SC4 to a predetermined position, a liquid transfer mechanism 5A having a plurality of liquid feed pump 19, . . . which feed a liquid to the sensor chips SC1 to SC4, alight projection optical system 7 which projects an excitation light 6 to a sensor chip at a detectable position DT (see FIG. 13A), a light-receiving optical system 8 which receives a fluorescence emitted from a sensor chip which has received the excitation light 6, a control means 9A which controls operations of the above-described each mechanism and optical system, storage means 10 used for the control means 9A, or the like.

Since the light-receiving optical system 8, the light projection optical system 7, and the chip information reading means have configurations similar to those of the first embodiment, the description thereof will be omitted.

[Sensor Chip]

First, since a sensor chip of the present embodiment is similar to the sensor chip 1 of the first embodiment except for the following points, the description of similar points will be omitted.

Sensor chips SC1 to SC4 of the second embodiment are different from the sensor chip 1 of the first embodiment, and store information about "a detection mode" instead of not having information about a dissociation constant and information about an order of a detection processing. FIGS. 14(A) to (D) illustrate the contents of information which four sensor chips SC1 to SC4 having different detection modes hold. A table of modes showing the contents of a processing of each detection mode is illustrated in FIG. 16.

Since the detection mode of the sensor chip SC1 of FIG. 14(A) is set to "1", as seen in a table (see FIG. 16) illustrating the contents of a detection processing for each detection mode, it is known that the sensor chip SC1 is a sensor chip on which a detection processing should be performed on a plurality of capture regions D to G fixed on a sensor unit in descending order of a dissociation constant. On the capture regions D to G, in a similar manner to the capture regions A to C of the first embodiment, a capturing body such as a primary antibody which captures a material to be detected is fixed on a sensor unit with the regions separated from each other by the type of the material.

Since the detection mode of the sensor chip SC2 of FIG. 14(B) is set to "2", as illustrated in FIG. 16, it is known that the sensor chip SC2 is a sensor chip in which a detection processing should be performed on each of the plurality of capture regions D to G fixed on a sensor unit of the sensor chip SC2 in ascending order of a detection threshold (cutoff value) represented by a concentration of a material to be detected (in ascending order of predicted measurement value of a fluorescence signal).

Since the detection mode of the sensor chip SC3 of FIG. 14(C) is set to "3", as illustrated in FIG. 16, it is known that the sensor chip SC3 is a sensor chip in which a detection processing should be performed on each of the plurality of capture regions D to G fixed on a sensor unit in descending order of accuracy of concentration detection of a material (antigen or the like) whose concentration is desired to be detected as accurately as possible (in descending order of required quantitativity).

Herein, the term "quantitativity" refers to how accurately a measurement value (concentration of a material to be detected) can be detected with respect to a true value (a value of a concentration of a material to be detected actually present in a specimen solution) (magnitude of error of measurement), and it can be said that the smaller the ratio of the measurement error is, "the higher the quantitativity (accuracy) is".

Specifically, when data for judging a condition of a subject is provided by quantifying a specific material to be detected, a required level of error of measured concentration differs, such as while one material to be detected a is desired to be detected with an error of measured concentration of ±10% with respect to its true value, another material to be detected b is desired to be detected with an error of measured concentration of ±100% with respect to its true value. When a required level of error of measured concentration is low as in the material to be detected a, it can be said that a quantitativity (accuracy) is high.

The above-described "true value" is, for example, obtained by the following.

First, a primary reaction and a secondary reaction (fluorescence color emission) are performed by using a reference solution in which the concentration of a material to be detected is known; a fluorescence intensity obtained in a secondary reaction at a point in time when an elapsed time from the start of an immunoassay reaction is the same is measured for each of a plurality of the reference solutions having different concentrations; a correlation (calibration curve) between the measurement value (fluorescence intensity) and a concentration of a material to be detected is prepared in advance; and this information is stored in the storage means 10 or the like of the immunoassay device 100A. Next, a measurement of a fluorescence intensity is actually performed by the immunoassay device 100A on a material to be detected in a specimen solution, and the measurement value (fluorescence intensity) is converted into a concentration by using the above-described calibration curve. A value of a concentration of a material to be detected measured in the same condition (a point in time from the start of detection is the same as a point in time of a measurement of a reference solution or the like) as when the above-described calibration curve is prepared is a true value. When the above-described measurement value is changed by changing (for example, a measurement is performed by changing a detection processing order) condition such as a timing of a measurement, a difference in the change is an error of measurement.

Since the detection mode of the sensor chip SC4 of FIG. 14(D) is set to "−" and information about an order of a detection processing is not present in the sensor chip, as illustrated in FIG. 16, it is known that the sensor chip SC4 is a sensor chip in which a detection processing should be performed on each of the plurality of capture regions D to G fixed on a sensor unit in an order in which a detection operation is completed in a time as short as possible (minimum time).

[Casing]

As illustrated in FIG. 13, the casing 3A of the immunoassay device 100A is provided with chip information reading means (not illustrated), an operation unit 22, a display unit 23, a print output unit 24, and the like. On the casing 3A of the immunoassay device 100A, as described above, slots 2B to 2E for inserting the sensor chips SC1 to SC4 are formed. The casing 3A is, for example, provided with known detection means similar to the above which detects whether the sensor chips SC1 to SC4 are inserted into the slots 2B to 2E or not.

[Control Means]

As illustrated in FIG. 13A, the control means 9A is a general personal computer or the like, which is connected to the above-described sensor chip transfer mechanism 4A, liquid transfer mechanism 5A, light projection optical system 7, light-receiving optical system 8, and each unit of the casing 3A (the operation unit 22, the display unit 23, the print output unit 24, and the like), or the like, and has a function of controlling these.

The control means 9A has the storage means 10, and the storage means 10 stores databases az1 to az3 (see FIG. 17 to FIG. 19), a mode table (see FIG. 16), a control program 35A (including those illustrated in FIG. 21 to FIG. 22) for performing an immunoassay method according to the present invention.

The control means 9A functions as each means (including detection processing order determination means) performing a detection preparation step S1A, a detection processing order determination step S2A, a liquid feed reaction step S3A, a detection processing step S4A, and an output step S5A. The control program 35A has a data structure for dealing with each item data of the chip information of the sensor chips SC1 to SC4 (see FIG. 15).

[Data Structure]

The data structure is constituted as what is called in a general program an array of a structure, which is for storing chip information or the like of a sensor chip which has been inserted into an immunoassay device. Since the data structure is similar to the data structure of the first embodiment illustrated in FIG. 8 except for the following points, description of the common part will be omitted.

While, in the first embodiment, "Dtc_Aln" for storing information representing an order of a detection processing of each capture region is used, a structure of data used in the second embodiment has, in place of "Dtc_Aln", "Dtc_Pri" for storing a priority of a detection processing and "Dtc_mode" for storing a detection mode (see FIG. 15).

[Database]

The storage means 10 stores, as described above, the databases az1 to az3 used for determining an order of a detection processing of each capture region.

The database az1 (see FIG. 17) stores data such as a name of a material to be detected, a first dissociation constant between a capture antibody and a material to be detected, a second dissociation constant between a material to be detected and a labeled antibody, and a relative value of a dissociation constant.

The database az1 is used for determining an order of a detection processing of each capture region fixed on a sensor unit of a sensor chip, and is one in which, when the larger of a first dissociation constant between a capture antibody of each of the capture regions D to G and a material to be detected to be captured by the capture antibody, and a second dissociation constant between the material to be detected and a labeled antibody to be bound to the material to be detected is selected, materials to be detected are arranged in descending order based on the selected dissociation constant.

The database az2 (see FIG. 18) stores data such as a name of a material to be detected and "a detection threshold" representing a detection cutoff value of a material to be detected. The database az2 is used for determining an order of a detection processing of the capture regions D to G fixed on a sensor unit of a sensor chip, and is one in which materials to be detected a to g are arranged in ascending order of the "detection threshold".

The database az3 (see FIG. 19) stores data such as a name of a material to be detected and a quantitativity (accuracy) required when a material to be detected is detected. The database az3 is used for determining an order of a detection processing of the capture regions D to G fixed on a sensor unit of a sensor chip, and is one in which materials to be detected a to g are arranged in ascending order of the "quantitativity (accuracy)".

[Mode Table]

A mode table (see FIG. 16), which is stored in the above-described storage means 10 as a database different from the above-described databases az1 to az3, at least stores a name of a database to be referred to for each mode. In an example of FIG. 16, the contents of a processing which is set for each mode is stored as a remark.

<Immunoassay Method>

In the following, an example in which an immunoassay method is performed by using the immunoassay device 100A of the second embodiment according to the present invention will be specifically described with reference mainly to FIG. 13 to FIG. 27.

[Detection Preparation Step]

In a step S1A-1 of the detection preparation step S1A (see FIG. 20), as illustrated in FIG. 21(A), whether the operation unit 22 in the casing 3A of the immunoassay device 100A is operated by a user to switch a test start button to ON or not is determined. When the determination is YES, the process proceeds to a step S1A-2, and when the determination is No, the process returns to the step S1A-1.

[Detection Preparation Step]

In the step S1A-2, the control means 9A determines whether each of the sensor chips SC1 to SC4 is inserted into each of the slots 2B to 2E or not based on information from detection means. When the sensor chip 1 is inserted and the determination is YES, the process proceeds to a step S1A-3, and when the sensor chip 1 is not inserted into each of the slots 2B to 2E and the determination is NO, the process returns to the step S1A-1.

In the step S1A-3, the control means 9A reads out information of a sensor chip from the information storage medium 14 of each of the sensor chips SC1 to SC4 which is inserted into each of the slots 2B to 2E.

In a step S1A-4, each information (see FIG. 14) of a sensor chip read out in the step S1A-3 is stored as an array element of a data structure of FIG. 15. A state after storing the information is illustrated in each of FIG. 23(A), FIG. 24(A), FIG. 25(A) and FIG. 26(A). A head address of an array element of each data structure of these sensor chips SC1 to SC4 is stored in an array *SCs of another data structure defining a pointer in the order of FIG. 23(A) to FIG. 26(A).

[Detection Processing Order Determination Step]

In a step S2A-1 of a detection processing order determination step S2A (see FIG. 20), as illustrated in FIG. 21(B), each data structure is updated in accordance with information such as detection modes ("1" to "3") stored in the sensor chips SC1 to SC4, or information which is not stored "−" (for convenience, no data is designated by "−") by referring to databases az1 to az3 or without reference.

In the step S2A-1, whether the detection mode is "1" or not is determined. When the detection mode is 1 and the determination is Yes, the process proceeds to a step S2A-2, and when the detection mode is not "1" and the determination is No, the process proceeds to a step S2A-3. Only the sensor chip SC1 whose detection mode is "1" proceeds to a processing of the step S2A-2.

In the step S2A-2, a processing of searching a row matching a name of material to be detected of a spot [0] "material d" for a database to be referred to az1 (see FIG. 17) with respect to the sensor chip SC1 (see FIG. 23(A)), and the fourth row is selected. "4" which is the order of the row is then stored in "Dtc_Pri" as information of a priority of a detection processing (see FIG. 23(B)). A similar processing is performed for spots [1] to [3] which are remaining array elements of the data structure, and each of "6", "7" and "2" is stored in "Dtc_Pri" (see FIG. 23(A) and FIG. 23(B) comparing to each other).

In the step S2A-3, whether the detection mode is "2" or not is determined. When the detection mode is "2" and the determination is Yes, the process proceeds to a step S2A-4, and when the detection mode is not "2" and the determination is No, the process proceeds to a step S2A-5. Only the sensor chip SC2 whose detection mode is "2" proceeds to a processing of the step S2A-4.

In the step S2A-4, a processing of searching a row matching a name of material to be detected of a spot [0] "material d" for a database to be referred to az2 (see FIG. 18) with respect to the sensor chip SC2 (see FIG. 24(A)), and the second row is selected. "2" which is the order of the row is then stored in "Dtc_Pri" as information of a priority of a detection processing (see FIG. 24(B)). A similar processing is performed for spots [1] to [3] which are remaining array elements of the structure, and each of "7", "6" and "4" is stored in "Dtc_Pri" (see FIG. 24A(B) and FIG. 24B(B)).

In the step S2A-5, whether the detection mode is "3" or not is determined. When the detection mode is "3" and the determination is Yes, the process proceeds to a step S2A-6, and when the detection mode is not "3" and the determination is No, the process proceeds to a step S2A-7. Only the sensor chip SC3 whose detection mode is "3" proceeds to a processing of the step S2A-6.

In the step S2A-6, a processing of searching a row matching a name of material to be detected of a spot [0] "material d" for a database to be referred to az3 (see FIG. 19) with respect to the sensor chip SC3 (see FIG. 25(A)), and the fourth row is selected. "4" which is the order of the row is then stored in "Dtc_Pri" as information of a priority of a detection processing (see FIG. 25(B)). A similar processing is performed for spots [1] to [3] which are remaining array elements of the structure, and each of "6", "7" and "3" is stored in "Dtc_Pri" (see FIG. 25(A) and FIG. 25(B) comparing to each other).

In the step S2A-7, whether a detection mode is present or not is determined. When a detection mode is not present and the determination is Yes, the process proceeds to a step S2A-8, and when some detection mode other than "1" to "3" is present and the determination is No, the process proceeds to a step S2A-9, and an error is displayed on the display unit 23.

In the step S2A-8, since a database to be referred to is not present, an order of a detection processing of each capture region such that an operation of a device is minimum is calculated with respect to the sensor chip SC5 (see FIG. 26(A)).

As a specific example, a route having a shortest shift distance for performing a detection processing for all capture regions is calculated from a coordinate position (x, y) on a sensor unit on which the optical detection means 21 is positioned and position information "S_Pos"(X, Y) of all capture regions, and an order of a capture region satisfying the route is stored in "Dtc_Pri" of the data structure.

Here, when an optical detection system is positioned on a base point P(0, 0) on a sensor chip at a point in time of starting of detection, as illustrated in FIG. 25(A) or (B), a route having the shortest distance for detecting all capture regions is in the order of capture region D→E→F→G, or the order of D→G→F→E (see FIGS. 27(D1) and (D2)). Accordingly, as illustrated in FIG. 26(A) and FIG. 26(B), each of "1", "2", "4" and "3" (i.e., "1", "4", "2" and "3") is set to "Dtc_Pri" of spots [0] to [3]. For all sensor chips, the step S2 is performed.

In a step S2A-10, an array of a data structure is sorted in ascending order of a priority (Dtc_Pri) of a detection processing set as above (see FIG. 23(C), FIG. 24(C), FIG. 25(C), FIG. 26(C-1), and FIG. 26(C-2)). In this state, an order of a detection processing is determined for each capture region.

[Liquid Feed Reaction Step]

In a cleaning step (see FIG. 21(c)) of a step S3A-1 of the liquid feed reaction step S3A (see FIG. 20), the sensor chip is shifted to a position where a liquid can be fed (see FIG. 13A), a buffer solution is fed by the liquid transfer mechanism 5A to remove a moisturing agent, and then, a processing of feeding a cleaning liquid is performed. After that, each of the sensor chips SC1 to SC4 is shifted to a detectable position DT (see FIG. 13A).

In a step S3A-2, the optical detection means 21 is shifted to a detection position of any one of the capture regions D to G of the sensor unit, and the excitation light cut filter 30 is evacuated from an optical axis. A plasmon enhancement angle is then measured, and the value is set as an incident angle (θ) which is used when the excitation light 6 is made incident on the metal thin film 12 in a detection processing described below with respect to the capture regions D to G (Dtc_EA). After this setting, the evacuated excitation light cut filter 30 is again inserted into an optical axis of the light-receiving optical system 8. The order of setting of the enhancement angle and the insertion of the excitation light cut filter 30 may be reversed. After the measurement of the plasmon enhancement angle for each capture region, measurement and setting of an optical blank value for each of the capture regions D to G are performed (Dtc_BL). Measurement and setting of an enhancement angle and measurement and setting of an optical blank value may be performed together for each of the capture regions D to G.

In a step S3A-3, each of the sensor chips SC1 to SC4 is again shifted to a position where a liquid can be fed (see FIG. 13A), a specimen solution is fed to the micro flow channel 15, and a material to be detected in a specimen solution is bound to an antibody of each of the capture regions D to G fixed on a sensor unit (not illustrated) of each of the sensor chips SC1 to SC4 to perform a primary reaction.

In a step S3A-4, a solution of an antibody labeled with a fluorescent material is fed to the micro flow channel 15, and the antibody labeled with a fluorescent material is bound to a material to be detected captured by each capture antibody of the sensor unit of each of sensor chips SC1 to SC4. After that, each of the sensor chips SC1 to SC4 is shifted to a detectable position DT.

[Detection Processing Step]

In a step S4A-1 (see FIG. 22) of the detection processing step S4A (see FIG. 20), an integer value m is set to 0.

In a step S4A-2, the m-th data structure is referred to. Specifically, by using a pointer *SCs defined in the step S1A-4, a structure is referred to. For example, when m=0, a data structure SC1 spot (see FIG. 23(A)) in an address stored in *SCs [0] is referred to. In a specific example, the order of an address of each data structure stored in the pointer *SCs is SC1 spot [ ] to SC4 spot [ ], but the order is not limited thereto.

In a step S4A-3, an integer value n is set to 0.

In a step S4A-4, the n-th element of an array of a data structure which is referred to is referred to. For example, when n=0, 0-th element (for example, when the sensor chip SC1 undergoes a processing, SC1 spot [0]) is referred to (see FIG. 23(C)).

In a step S4A-5, the optical detection means 21 and a capture region of the element are aligned based on position information of a capture region included in the n-th element. For example, when m=0 and when the sensor chip SC1 undergoes a processing and n=0, the alignment is performed based on position information (SC1 spot [0] .S_Pos)=(2, 2) of a capture region included in the 0-th element (see FIG. 23(C), partly not illustrated).

In a step S4A-6, a detection processing of the aligned capture region is started, and the process proceeds to the step S4A-7 to start a timer.

In a step S4A-8, whether a time (TL) from the start of the timer is longer than a measurement time (spot [n] .Dtc_Tim) of an array element of a data structure which is referred to or not is determined. In a specific example, when m=0 and n=0, whether SC1 spot [0] .Dtc_Tim=10 seconds (see FIG. 23(C)) has elapsed or not is determined. When the determination is No in which the time is not longer than the measurement time, the process returns to the step S4A-8. On the other hand, the determination is Yes in which the time is longer than the measurement time, the detection processing is terminated and the process proceeds to a step S4A-9.

In a step S4A-9, a timer is stopped and reset, and the process proceeds to step S4A-10, and a detection processing for a spot of a processing target is terminated.

In a step S4A-11, whether a capture region which has not undergone a detection processing is present or not (whether an array element of the n+1-th data structure is present or not) is determined, and when the determination is Yes in which the capture region is present, the process proceeds to S4A-12 in which the integer value n is incremented, and returns to the step S4A-4. On the other hand, when the determination is No in which the capture region which has not undergone a detection processing is not present, the process proceeds to a step S4A-13.

As described above, when the process returns to the step S4A-4, a processing similar to the above-described processing is repeated for each capture region of sensor chip which undergoes a processing until an array element of a structure of a spot which is referred to disappears. By this, each of the capture regions D to G in a sensor unit undergoes a detection processing sequentially as illustrated in each of FIGS. 27(A) to (D2) in ascending order of the number of an array element of the data structure which is referred to, in other words, in accordance with an order of a detection processing determined in the detection processing order determination step.

On the other hand, when the determination is Yes in which n+1-th array element is present and an undetected spot is not present, the process proceeds to the step S4A-13.

In the step S4A-13, whether all sensor chips undergo a detection processing or not is determined. Specifically, whether an array element of the m+1-th *Scs is present or not is examined, and when a sensor chip which does not undergo a processing is present, the process proceeds to a step S4A-14 to increment m, and the process returns to the step S4A-2. By this, a processing similar to the above is repeated until a structure of a sensor chip which should undergo a processing disappears.

[Output Step]

In an output step S5A (see FIG. 20), an output processing in which the above-described detected result is printed out by the print output unit 24 or displayed on the display unit 23 is performed.

In the following, operations and effects of an immunoassay method and an immunoassay system of the second embodiment according to the present invention will be described.

(1) When information about an order of a detection processing is about ascending order of a detection threshold of a material to be detected, in other words, ascending order of a predicted measurement value of a signal of a fluorescence emitted from a capture region, an item of a material to be detected in which a value measured by a detection processing is weak and a detection with a high sensitivity is needed preferentially undergoes a detection processing.

(2) When information for determining an order of a detection processing is stored not only in the information storage medium 14 of the sensor chips SC1 to SC4 but also in the storage means 10 of the immunoassay device 100A, information of an order of a detection processing of a sensor chip can be changed in a collective manner by editing a database stored in the storage means 10 of the immunoassay device 100A without individually editing information about an order of a detection processing stored in the sensor chips SC1 to SC4 for each sensor chip. By referring to information on a database stored in the storage means 10 of the immunoassay device 100A, only a small piece of information such as a name of a material to be detected may be provided on the sensor chips SC1 to SC4, and a bar code or the like may be provided with a small amount of information, which is convenient.

(3) When information about an order of a detection processing is information representing a degree of necessity of detection accuracy (in other word, in ascending order of the width of an error of a measured concentration (± %) which is tolerated in a quantitative analysis), a capture region undergoes a detection processing in descending order of the degree of necessity of a detection accuracy of a material to be detected captured by a capture region, more appropriate data is provided with respect to an item to be detected requiring a more accurate data.

(4) When information about an order of a detection processing is not present in a sensor chip, a detection processing is performed in an order in which an operation of a device is minimum, and therefore, a time for the detection processing can be shortened.

As described above, an immunoassay method and an immunoassay system according to the present invention is described in detail along with the embodiments, the present invention is not limited to the above-described embodiment, and a design change will be allowed without departing from the gist of the present invention described in CLAIMS.

For example, while in the second embodiment, the sensor chips SC1 to SC4 undergo a detection processing by providing the slots 2B to 2E, the number of sensor chips on which a processing is performed or the number of slots is not limited to those in the above-described embodiments.

DESCRIPTION OF SYMBOLS 1 sensor chip
2A to 2F slot
3, 3A casing
4 sensor chip transfer mechanism
5, 5A liquid transfer mechanism
6 excitation light
7 light projection optical system
8 light-receiving optical system
9, 9A control means
10 storage means
11 dielectric member
12 metal thin film
13 micro flow channel component member
14 information storage medium
15 micro flow channel
16 liquid discharge/suction unit
17 liquid mixing unit
18 hermetic seal
19 liquid feed pump
20 sensor unit
21 light detection means (optical detection means)
22 operation unit
23 display unit
24 print output unit
25 chip information reading mechanism
26 light source
27 angle scanning mechanism
28 light source control mechanism
29 optical lens group
30 excitation light cut filter
31 sensor control mechanism
32 position switch mechanism
33 liquid feed pump drive mechanism
34 chemical well
35, 35A control program
36 optical unit
100, 100A immunoassay device (device for detection processing)
az1 to az3 database
P base point
SC1 to SC4 sensor chip

The invention claimed is:

1. An immunoassay method using a sensor chip on which a plurality of capture regions are arranged separately from each other, wherein the plurality of capture regions capture a material to be detected by a first capturing body, wherein the plurality of capture regions are formed by using a different type of first capturing body depending on the type of a material to be detected to be captured, the method comprising:
bringing a sample into contact with the sensor chip so that a material is captured by the first capturing body in the plurality of capture regions;
determining a detection processing order in which a detection processing is to be individually performed for each of the respective capture regions, wherein the detection processing order is determined based on information about a detection processing order of the plurality of the capture regions; and
individually performing the detection processing for each of the capture regions in the determined detection processing order, wherein the detection processing comprises individually irradiating each capture region and detecting fluorescence emitted from the irradiated capture region, in the determined detection processing order.

2. The immunoassay method according to claim 1, wherein the information about a detection processing order is information stored in the sensor chip, or information stored in a device in which a detection processing is performed which is referred to corresponding to information stored in the sensor chip.

3. The immunoassay method according to claim 2, wherein the information about a detection processing order is information about a dissociation constant of the material to be detected.

4. The immunoassay method according to claim 2, wherein the information about a detection processing order is information about a type of the material to be detected.

5. The immunoassay method according to claim 2, wherein the information about a detection processing order is information in which the detection processing order is determined in advance.

6. The immunoassay method according to claim 1, wherein the information about a detection processing order is information about a dissociation constant of the material to be detected.

7. The immunoassay method according to claim 6, wherein information about a dissociation constant of the material to be detected is a first dissociation constant between the material to be detected and the first capturing body or a second dissociation constant between the material to be detected and a second capturing body labeled with a fluorescent material.

8. The immunoassay method according to claim 6, wherein the information about a detection processing order is information about a type of the material to be detected.

9. The immunoassay method according to claim 7, wherein the information about a detection processing order is information about a type of the material to be detected.

10. The immunoassay method according to claim 6, wherein the information about a detection processing order is information in which the detection processing order is determined in advance.

11. The immunoassay method according to claim 1, wherein the information about a detection processing order is information about a type of the material to be detected.

12. The immunoassay method according to claim 1, wherein the information about a detection processing order is information in which the detection processing order is determined in advance.

13. The immunoassay method according to claim 1, wherein the information about a detection processing order is information representing a degree of necessity of detection accuracy.

14. The immunoassay method according to claim 1, wherein the information about a detection processing order is ascending order of a predicted measurement value of a fluorescence signal.

15. The immunoassay method according to claim 1, wherein, when information stored in the sensor chip is not present, a detection processing order is determined such that a total time for performing the detection processing for all of the plurality of capture regions is minimized.

16. The immunoassay method according to claim 1, further comprising simultaneously performing capturing of the material to be detected by the first capturing body and performing fluorescent labeling of a material to be detected by a second capturing body in the plurality of capture regions.

17. The immunoassay method according to claim 1, wherein the detection processing comprises detecting, in each of the plurality of capture regions, a fluorescence signal by a surface plasmon-field enhanced fluorescence spectroscopy.

* * * * *